US011065422B2

(12) United States Patent
Kassab et al.

(10) Patent No.: US 11,065,422 B2
(45) Date of Patent: Jul. 20, 2021

(54) DEVICES, SYSTEMS, AND METHODS USEFUL TO ENGAGE TISSUE USING SUCTION AND TO PERFORM MEDICAL PROCEDURES DURING SUCTIONAL ENGAGEMENT

(71) Applicants: Ghassan S. Kassab, La Jolla, CA (US); Matthew Phillips, Carlsbad, CA (US); H. Toby Markowitz, Roseville, MN (US)

(72) Inventors: Ghassan S. Kassab, La Jolla, CA (US); Matthew Phillips, Carlsbad, CA (US); H. Toby Markowitz, Roseville, MN (US)

(73) Assignee: CVDevices, LLC, San Diego, CA (US)

( * ) Notice: Subject to any disclaimer, the term of this patent is extended or adjusted under 35 U.S.C. 154(b) by 300 days.

(21) Appl. No.: 15/821,825

(22) Filed: Nov. 23, 2017

(65) Prior Publication Data

US 2018/0085554 A1    Mar. 29, 2018

Related U.S. Application Data

(63) Continuation-in-part of application No. 15/570,222, filed as application No. PCT/US2016/029893 on Apr. 28, 2016.

(Continued)

(51) Int. Cl.
*A61M 25/00* (2006.01)
*A61B 17/34* (2006.01)
(Continued)

(52) U.S. Cl.
CPC ... *A61M 25/0067* (2013.01); *A61B 17/00491* (2013.01); *A61B 17/3401* (2013.01);
(Continued)

(58) Field of Classification Search
CPC ...... A61M 2025/0057; A61M 25/0026; A61M 25/0067; A61M 25/0084; A61M 25/06; A61M 25/09; A61M 2025/0681; A61M 2025/0175; A61M 25/003; A61M 2025/0089; A61M 25/0662; A61M 16/0463; A61M 2025/091; A61M 2039/0009; A61B 17/3401; A61B 17/3403; A61B 17/3415; A61B 17/3478;
(Continued)

(56) References Cited

U.S. PATENT DOCUMENTS 9,629,979 B2 * 4/2017 Gunday ............ A61M 25/0084
2005/0261662 A1 * 11/2005 Palasis ............... A61B 18/1492
604/506

(Continued)

*Primary Examiner* — Quynh-Nhu H. Vu
(74) *Attorney, Agent, or Firm* — Reichel Stohry Dean LLP; Mark C. Reichel; Natalie J. Dean

(57) ABSTRACT

Devices, systems, and methods useful to engage tissue using suction and to perform medical procedures during sectional engagement. The present disclosure includes disclosure of a tension apparatus, comprising an elongated portion; and a head portion at a distal end of the elongated portion, the head portion comprising one or more arms, whereby a suction lumen extending along the elongated portion and the one or more arms terminates at one or more suction openings at each of the one or more arms.

14 Claims, 24 Drawing Sheets

Related U.S. Application Data

(60) Provisional application No. 62/425,772, filed on Nov. 23, 2016, provisional application No. 62/312,642, filed on Mar. 24, 2016, provisional application No. 62/293,187, filed on Feb. 9, 2016, provisional application No. 62/153,788, filed on Apr. 28, 2015.

(51) Int. Cl.
| | |
|---|---|
| *A61B 17/00* | (2006.01) |
| *A61M 25/09* | (2006.01) |
| *A61M 25/06* | (2006.01) |
| *A61B 17/30* | (2006.01) |
| *A61B 18/02* | (2006.01) |
| *A61B 18/00* | (2006.01) |
| *A61B 18/14* | (2006.01) |

(52) U.S. Cl.
CPC ..... *A61B 17/3478* (2013.01); *A61M 25/0026* (2013.01); *A61M 25/0084* (2013.01); *A61B 17/3403* (2013.01); *A61B 17/3415* (2013.01); *A61B 18/02* (2013.01); *A61B 18/14* (2013.01); *A61B 2017/00026* (2013.01); *A61B 2017/00044* (2013.01); *A61B 2017/00084* (2013.01); *A61B 2017/00247* (2013.01); *A61B 2017/308* (2013.01); *A61B 2018/00291* (2013.01); *A61M 25/06* (2013.01); *A61M 25/09* (2013.01); *A61M 2025/0057* (2013.01)

(58) Field of Classification Search
CPC .......... A61B 18/14; A61B 2017/00247; A61B 2017/308; A61B 2018/00291; A61B 17/0218; A61B 17/0293; A61B 17/3417; A61B 17/3421; A61B 17/3431; A61B 2017/00867; A61B 2017/3456; A61B 2017/3484; A61B 2017/3492
See application file for complete search history.

(56) References Cited

U.S. PATENT DOCUMENTS

| | | | |
|---|---|---|---|
| 2007/0156010 A1* | 7/2007 | Aboul-Hosn | A61M 1/3659 600/18 |
| 2014/0276051 A1* | 9/2014 | Hoffman | A61B 17/3417 600/439 |

* cited by examiner

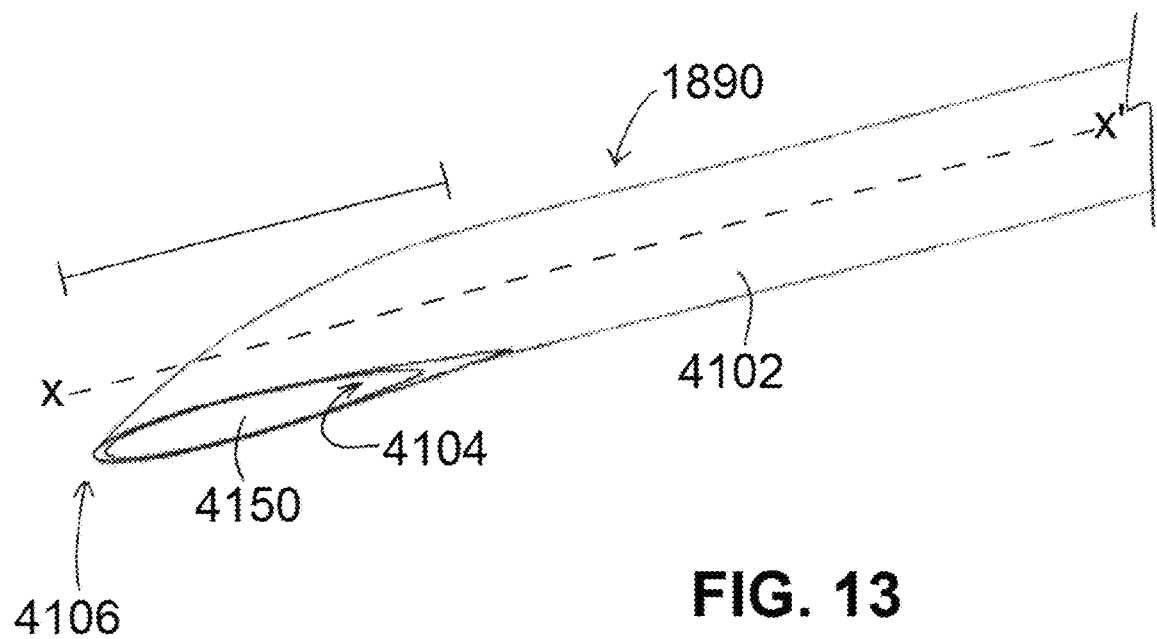
FIG. 13
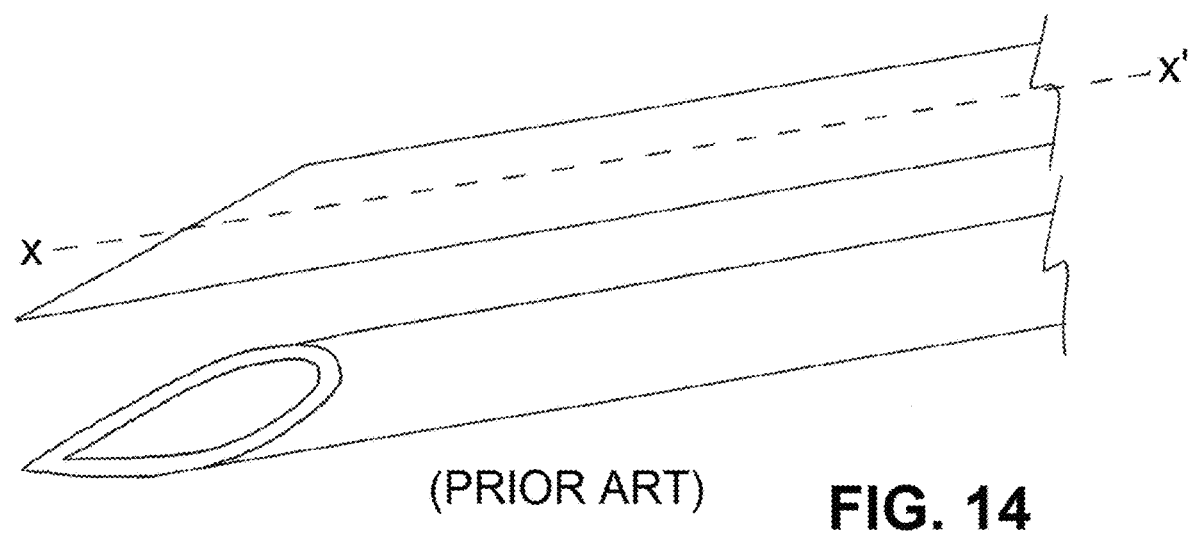
(PRIOR ART) FIG. 14

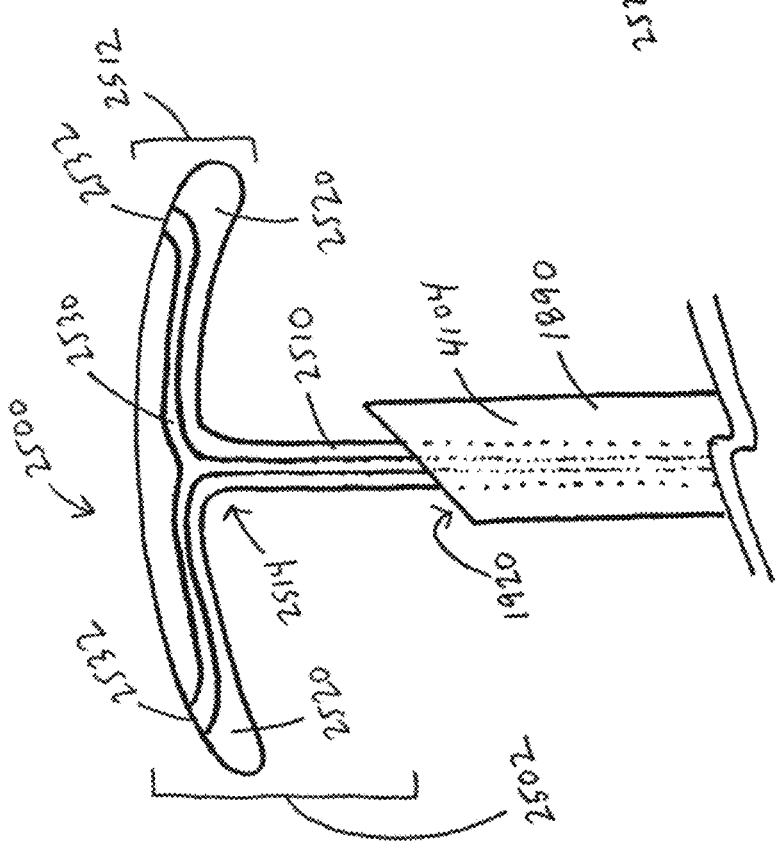
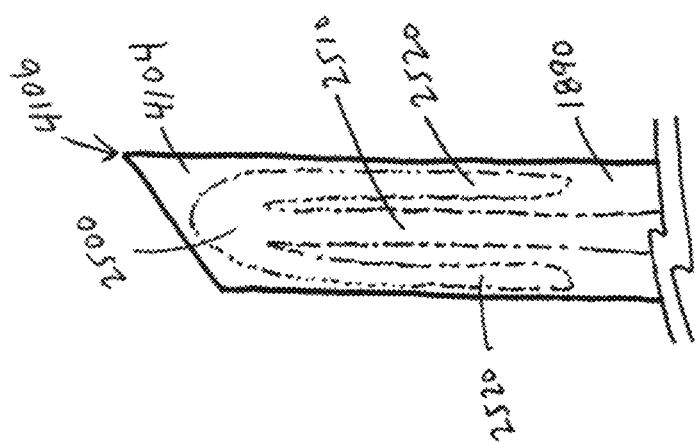
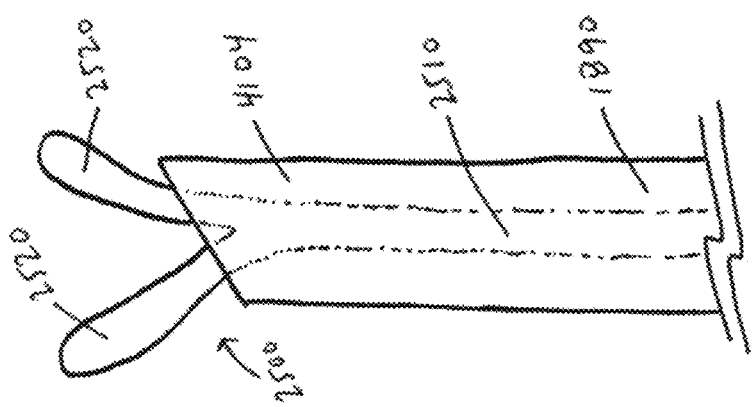
FIG. 25A
FIG. 25B
FIG. 25C

FIG. 22

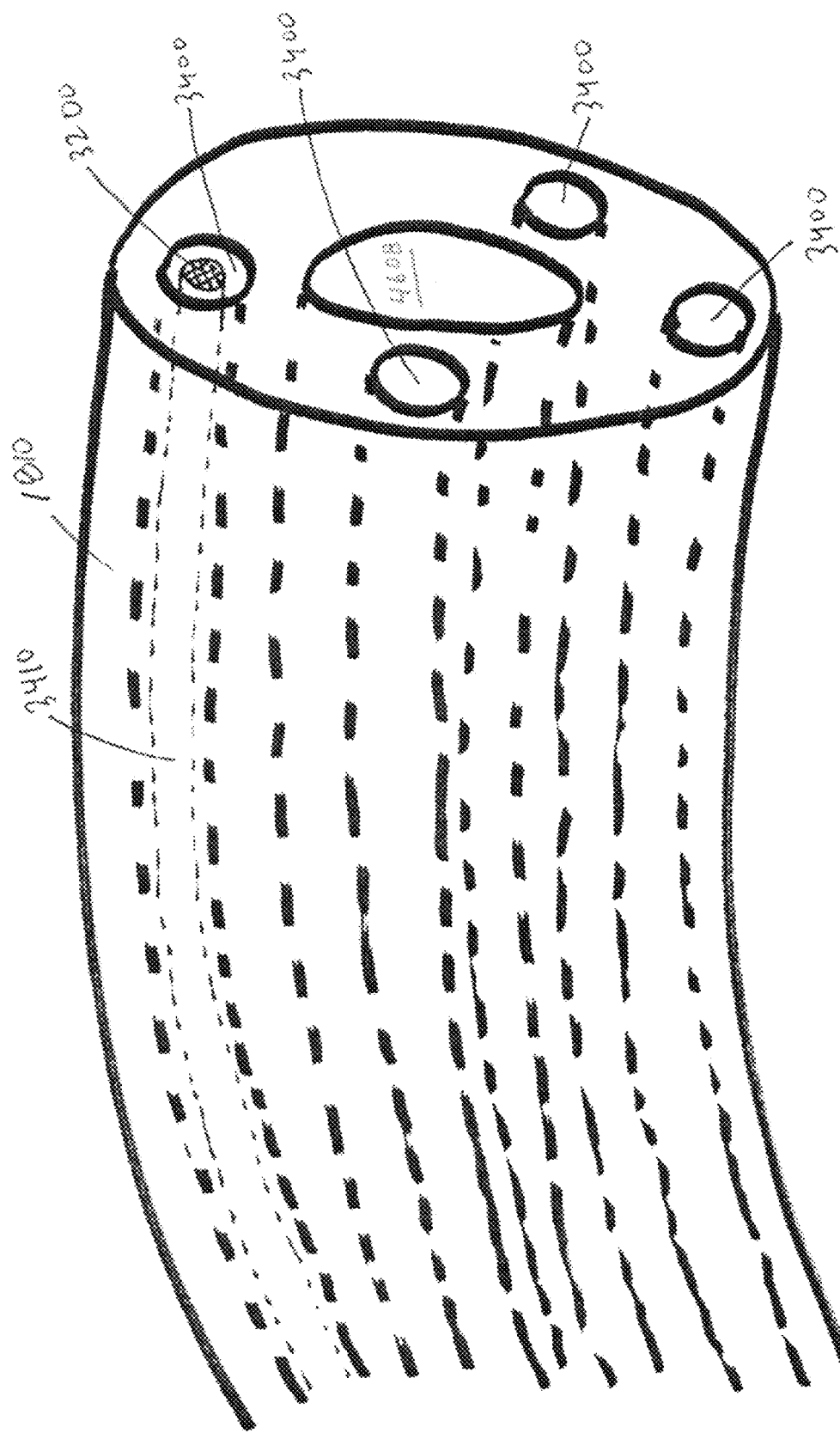

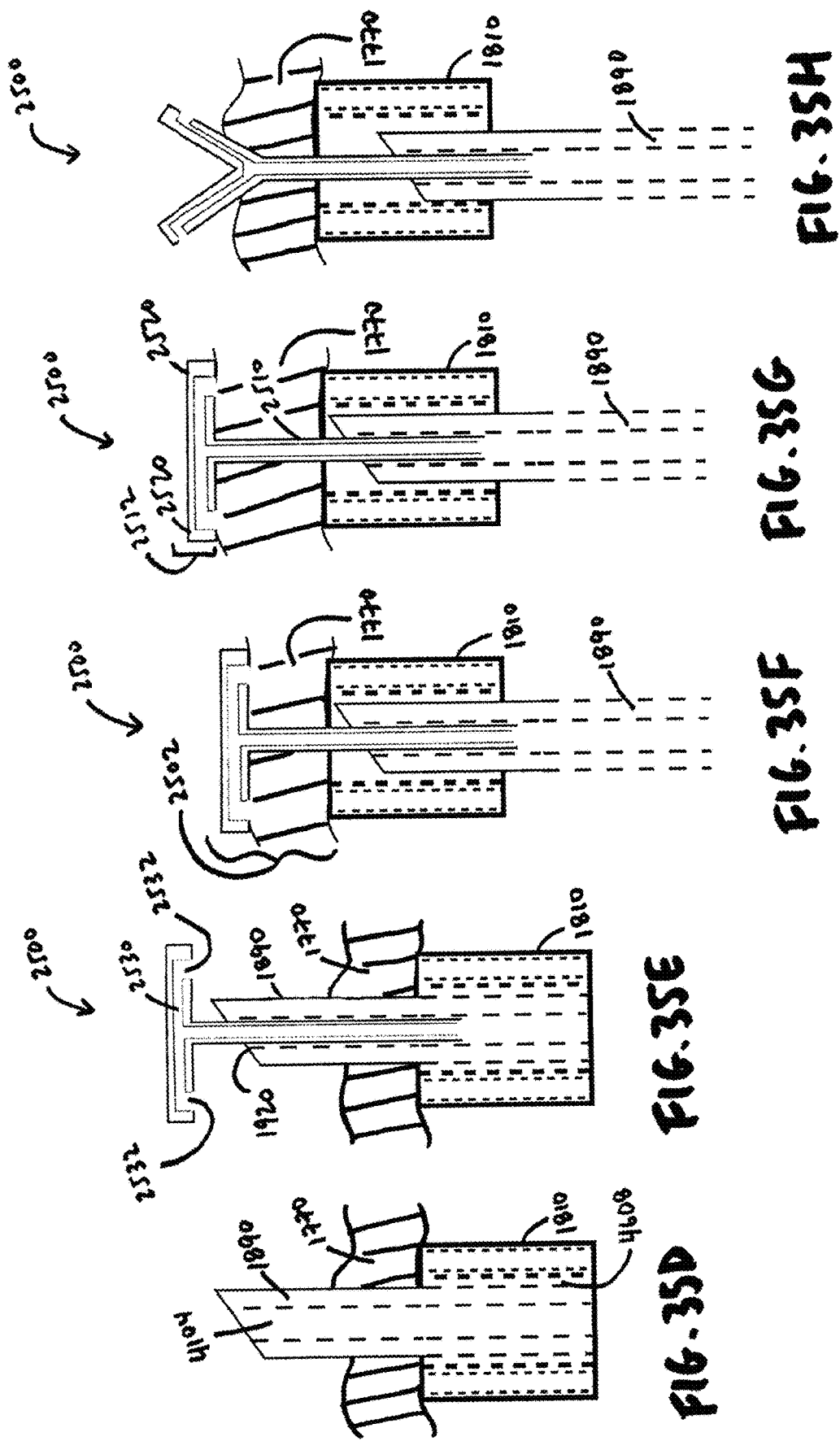

DEVICES, SYSTEMS, AND METHODS USEFUL TO ENGAGE TISSUE USING SUCTION AND TO PERFORM MEDICAL PROCEDURES DURING SUCTIONAL ENGAGEMENT

PRIORITY AND INCORPORATION BY REFERENCE

The present application a) is related to, and claims the priority benefit of, U.S. Provisional Patent Application Ser. No. 62/425,772, filed Nov. 23, 2016, and b) is related to, claims the priority benefit of, and is a U.S. continuation-in-part patent application of, U.S. patent application Ser. No. 15/570,222, filed Oct. 27, 2017, which is related to, claims the priority benefit of, and is a U.S. § 317 National Stage application of, PCT Patent Application Serial No. PCT/US2016/029893, filed Apr. 28, 2016, which is related to, and claims the priority benefit of, i) U.S. Provisional Patent Application Ser. No. 62/153,788, filed Apr. 28, 2015, ii) U.S. Provisional Patent Application Ser. No. 62/293,187, filed Feb. 9, 2016, and iii) U.S. Provisional Patent Application Ser. No. 62/312,642, filed Mar. 24, 2016, the contents of which are hereby incorporated by reference in their entirety into this disclosure. The contents of U.S. Pat. No. 8,328,752 of Kassab et al., issued Dec. 11, 2012, are also hereby incorporated by reference in their entirety into this disclosure.

BACKGROUND

Over time, and due to various factors, walls of various mammalian luminal organs may become substantially, and potentially detrimentally, thin. In the case of aneurysms for example, a thin vessel wall causes the vessel to protrude due to pressure therein, whereby rupture of the aneurysm can be extremely harmful, if not fatal.

In view of the same, the use of materials, and methods to deliver the same, into a wall of a mammalian vessel to improve the structural integrity thereof, would be appreciated in the medical arts and marketplace.

BRIEF SUMMARY

The present disclosure includes disclosure of materials for introduction into a wall of a mammalian luminal organ so to improve the overall internal structural integrity of the same, reduce stress, and/or reduce or eliminate the risk of rupture. Said materials may comprise one or more non-degradable, non-inflammatory biopolymers including, but not limited to, one or more of alginate, polytetrafluoroethylene (PTFE), and an elastomer, such as, for example, silicone elastomer, polyurethane, butyl rubber, and ethylene-propylene rubber, for example.

The present disclosure also includes disclosure of methods for introducing materials into a wall of a mammalian luminal organ so to improve the overall internal structural integrity of the same, reduce stress, and/or reduce or eliminate the risk of rupture. Furthermore, the present disclosure includes disclosure of methods of medical treatment, comprising the introduction of a quantity of a material into a wall of a mammalian luminal organ. Said methods of medical treatment may comprise the introduction of one or more quantities of one or more materials into a wall of a mammalian luminal organ.

The present disclosure includes disclosure of treating a patient having an aneurysm, comprising the introduction of one or more quantities of one or more materials into a wall of a blood vessel at the aneurysm. The present disclosure also includes disclosure of treating a patient having a thin bladder wall, comprising the introduction of one or more quantities of one or more materials into the thin bladder wall. In addition, the present disclosure includes disclosure of treating a patient having a thin esophageal wall, comprising the introduction of one or more quantities of one or more materials into the thin esophageal wall.

The present disclosure further includes disclosure of delivery mechanisms for delivering a material into a wall of a mammalian luminal organ.

In an exemplary embodiment of a system of the present disclosure, the system comprises one or more of the following: an engagement catheter, a skirt or suction cup, a delivery catheter, a needle, and/or a wire, as described and shown herein. Said systems, in various embodiments, are configured to deliver a liquid material, such as alginate, to a tissue of interest, such as cardiac tissue, to treat heart failure.

The present disclosure includes disclosure of a method for reinforcing a wall of a luminal organ, comprising the steps of inserting at least part of a needle into a blood vessel of a patient, advancing a distal end of the needle within the blood vessel to a location adjacent to a wall of a luminal organ of interest, piercing the wall of the luminal organ using the needle so that a tip of the needle is present within the wall of the luminal organ, injecting a substance through the needle and out of a distal portion of the needle so that at least some of the substance is present outside of the needle and inside of the wall of the luminal organ to reinforce the wall of the luminal organ, and withdrawing the distal portion of the needle from the wall of the luminal organ.

The present disclosure includes disclosure of a method for reinforcing a wall of a luminal organ, wherein the step of inserting is preceded by the steps of inserting a guidewire into the blood vessel, advancing a distal end of the guide wire within the blood vessel, advancing at least part of an engagement catheter over the guidewire and into the blood vessel, wherein the step of inserting is performed by inserting the at least part of the needle into the at least part of the engagement catheter which is then present within the blood vessel of the patient.

The present disclosure includes disclosure of a method for reinforcing a wall of a luminal organ, wherein the step of injecting is performed to inject a substance selected from the group consisting of stem cells, a polymer, an elastomer, a drug/medicament, cells other than stem cells, and a solution.

The present disclosure includes disclosure of a method for reinforcing a wall of a luminal organ, wherein the step of advancing the at least part of the engagement catheter over the guidewire and into the blood vessel is performed so that a distal end of the engagement catheter contacts the wall of the luminal organ and further comprises the step of providing suction through a lumen of the engagement catheter so that the distal end of the engagement catheter suctionally engages the wall of the luminal organ.

The present disclosure includes disclosure of a method for reinforcing a wall of a luminal organ, wherein the step of injecting is performed while the suction is being provided through the lumen of the engagement catheter.

The present disclosure includes disclosure of a method for reinforcing a wall of a luminal organ, wherein the step of advancing the at least part of the engagement catheter over the guidewire and into the blood vessel is performed while a sheath is at least partially present around the engagement catheter.

The present disclosure includes disclosure of a method for reinforcing a wall of a luminal organ, wherein the engagement catheter comprises a suction cup at a distal end of the engagement catheter, and wherein movement of the sheath relative to the engagement catheter allows the suction cup to be exposed outside of the sheath so that the suction cup can expand.

The present disclosure includes disclosure of a method for reinforcing a wall of a luminal organ, wherein the step of advancing the at least part of the engagement catheter over the guidewire and into the blood vessel is performed so that the suction cup of the engagement catheter contacts the wall of the luminal organ and further comprises the step of providing suction through a lumen of the engagement catheter so that the suction cup of the engagement catheter suctionally engages the wall of the luminal organ.

The present disclosure includes disclosure of a method for reinforcing a wall of a luminal organ, wherein when performing the step of injecting the substance through the needle and out of the distal portion of the needle, and substance that is injected out of the distal portion of the needle and not into the wall of the luminal organ would be removed from the patient via suction through the lumen of the engagement catheter.

The present disclosure includes disclosure of a method for reinforcing a wall of a luminal organ, further comprising the step of removing any of the substance that may leak from the wall of the luminal organ after the distal portion of the needle is withdrawn from the wall of the luminal organ via suction through the lumen of the engagement catheter.

The present disclosure includes disclosure of a method for reinforcing a wall of a luminal organ, wherein the step of piercing the wall of the luminal organ is performed to pierce a wall of a myocardium, and wherein the step of injecting the substance through the needle and out of the distal portion of the needle is performed to inject the at least some of the substance into the wall of the myocardium.

The present disclosure includes disclosure of a method for reinforcing a wall of a luminal organ, wherein the needle has at least a first distal aperture and at least a second distal aperture defined within the needle at the distal portion along a relative sidewall of the needle, and wherein the step of injecting is performed to inject the at least some the substance through the needle and out of the first distal aperture and the second distal aperture.

The present disclosure includes disclosure of a method for reinforcing a wall of a luminal organ, wherein the needle has a first distal aperture defined within the needle at a distal tip of the needle along a relative sidewall of the needle, wherein the first distal aperture is relatively curved at a distal portion of the first distal aperture and tapers inward toward a distal portion of the first distal aperture, and wherein the step of injecting is performed to inject the at least some the substance through the needle and out of the first distal aperture.

The present disclosure includes disclosure of a method for reinforcing a wall of a luminal organ, wherein the needle has a curved distal portion and a first distal aperture defined within the needle along at least part of the curved distal portion, and wherein the step of injecting is performed to inject the at least some the substance through the needle and out of the first distal aperture in a direction other than a direction defined by an axis of a portion of the needle proximal to the curved distal portion.

The present disclosure includes disclosure of a method for reinforcing a wall of a luminal organ, comprising the steps of inserting at least part of a system into a blood vessel of a patient, the system comprising a needle positioned within a lumen of an engagement catheter having a suction cup at its distal end, advancing the at least part of the engagement catheter within the blood vessel so that the suction cup of the engagement catheter contacts a wall of the luminal organ, providing suction through a lumen of the engagement catheter so that the suction cup of the engagement catheter suctionally engages the wall of the luminal organ, piercing the wall of the luminal organ, while under suction through the lumen of the engagement catheter, using the needle so that a tip of the needle is present within the wall of the luminal organ, injecting a substance through the needle and out of a distal portion of the needle so that at least some of the substance is present outside of the needle and inside of the wall of the luminal organ to reinforce the wall of the luminal organ.

The present disclosure includes disclosure of a method for reinforcing a wall of a luminal organ, wherein the step of advancing the at least part of the engagement catheter is performed while a sheath is at least partially present around the engagement catheter, and wherein movement of the sheath relative to the engagement catheter allows the suction cup to be exposed outside of the sheath so that the suction cup can expand.

The present disclosure includes disclosure of a method for reinforcing a wall of a luminal organ, comprising the steps of inserting at least part of a system into a blood vessel of a patient, the system comprising a needle positioned within a lumen of an engagement catheter having a suction cup at its distal end, advancing the at least part of the engagement catheter within the blood vessel so that the suction cup of the engagement catheter contacts a wall of a myocardium, providing suction through a lumen of the engagement catheter so that the suction cup of the engagement catheter suctionally engages the wall of the myocardium, piercing the wall of the myocardium, while under suction through the lumen of the engagement catheter, using the needle so that a tip of the needle is present within the wall of the myocardium, injecting a first substance through the needle and out of a distal portion of the needle so that at least some of the first substance is present outside of the needle and inside of the wall of the myocardium to reinforce the wall of the myocardium to treat the patient. The present disclosure includes disclosure of a method for reinforcing a wall of a luminal organ, wherein the step of injecting is performed to inject a first substance selected from the group consisting of stem cells, a polymer, an elastomer, a drug/medicament, cells other than stem cells, and a solution. The present disclosure includes disclosure of a method for reinforcing a wall of a luminal organ, wherein the step of injecting is performed to inject alginate into the wall of the myocardium. The present disclosure includes disclosure of a method for reinforcing a wall of a luminal organ, wherein the method further comprises the step of injecting a first substance through the needle and out of a distal portion of the needle so that at least some of the first substance is present outside of the needle and inside of the wall of the myocardium. The present disclosure includes disclosure of a method for reinforcing a wall of a luminal organ, wherein the step of injecting a second substance is performed to inject saline into the wall of the myocardium. The present disclosure includes disclosure of a method for reinforcing a wall of a luminal organ, wherein the step of injecting is performed to inject the substance having a first ionic content, and wherein the step of injecting the second substance is performed in inject the second substance having a second ionic content differing from the first ionic content.

The present disclosure includes disclosure of a tension apparatus, comprising an elongated portion; and a head portion at a distal end of the elongated portion, the head portion comprising one or more arms, whereby a suction lumen extending along the elongated portion and the one or more arms terminates at one or more suction openings at each of the one or more arms.

The present disclosure includes disclosure of a tension apparatus, wherein when vacuum is applied through the suction lumen, the one or more arms contacting a tissue can become suctionally attached to the tissue.

The present disclosure includes disclosure of a tension apparatus, configured to fit at least partially within a needle, whereby a distal portion of the tension apparatus can extend out of a needle aperture of the needle.

The present disclosure includes disclosure of a tension apparatus, wherein the one or more arms are configured to bend so that during delivery of the tension apparatus within a needle, the one or more arms are next to a portion of the elongated portion.

The present disclosure includes disclosure of a tension apparatus, wherein the one or more arms are configured to bend so that during retraction of the tension apparatus within a needle, the one or more arms are distal to the elongated portion.

The present disclosure includes disclosure of a tension apparatus, configured so that when positioned at least partially within a needle that punctures a first tissue, the one or more arms can extend out of a needle aperture of the needle distal to the first tissue and suctionally attach to a second tissue distal to the first tissue under vacuum.

The present disclosure includes disclosure of a tension apparatus, wherein the one or more suction openings are distally located along the one or more arms so that the one or more suction openings can contact a tissue located distal to the one or more arms.

The present disclosure includes disclosure of a tension apparatus, wherein the one or more suction openings are proximally located along the one or more arms so that the one or more suction openings can contact a tissue located proximal to the one or more arms.

The present disclosure includes disclosure of a tension apparatus, forming part of a system, the system further comprising a needle configured to at least partially enclose the tension apparatus.

The present disclosure includes disclosure of a tension apparatus, forming part of the system, the system further comprising an engagement catheter configured to at least partially enclose the needle.

The present disclosure includes disclosure of a method, comprising introducing a needle into a mammalian body, the needle having at least a portion of a tension apparatus therein, the tension apparatus comprising an elongated portion, and a head portion at a distal end of the elongated portion, the head portion comprising one or more arms, whereby a suction lumen extending along the elongated portion and the one or more arms terminates at one or more suction openings at each of the one or more arms; advancing the tension apparatus within the needle so that the head portion extends out of a needle aperture at a distal end of the needle, said advancement causing the one or more arms to extend outward relative to the elongated portion; positioning the one or more arms adjacent to a tissue so that the one or more suction openings are located at the tissue; and applying suction through the suction lumen so to cause the one or more arms to suctionally engage the tissue at the one or more suction openings.

The present disclosure includes disclosure of a method, wherein the tissue is located distal to the one or more arms relative to the elongated portion, and wherein the step of positioning is performed to distally advance the one or more arms toward the tissue so that the one or more arms contact the tissue.

The present disclosure includes disclosure of a method, wherein the tissue is located proximal to the one or more arms relative to the one or more arms, and wherein the step of positioning is performed to proximally retract the one or more arms toward the tissue so that the one or more arms contact the tissue.

The present disclosure includes disclosure of a method, further comprising the step of performing an ablation procedure to the tissue using an ablation element of an ablation device while the one or more arms suctionally engage the tissue.

The present disclosure includes disclosure of a method, further comprising the step of discontinuing suction through the suction lumen.

The present disclosure includes disclosure of a method, further comprising the step of retracting the one or more arms of the tension apparatus into the needle, whereby the one or more arms within the needle are located proximal to the elongated portion of the tension apparatus.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 10, 11, 12, and 13 show perspective views of distal portion of needle, according to exemplary embodiments of the present disclosure;

FIG. 14 shows side and perspective views of prior art needles;

FIG. 25A shows a portion of a tension apparatus extending from a needle, such as when in use, according to an exemplary embodiment of the present disclosure;

FIG. 25B shows a portion of a tension apparatus positioned within a needle, such as during delivery of the tension apparatus, according to an exemplary embodiment of the present disclosure;

FIG. 25C shows a portion of a tension apparatus extending from a needle, such as during withdrawal of the tension apparatus into the needle, according to an exemplary embodiment of the present disclosure;

FIGS. 27 and 28 show cutaway views of a distal portions of engagement catheters with needles positioned therein and having least one internal sensor, according to exemplary embodiments of the present disclosure;

FIG. 34 shows a distal portion of an engagement catheter having a delivery lumen, a plurality of peripheral lumens, and a conductive cable or wire, according to an exemplary embodiment of the present disclosure;

FIG. 35D shows a needle penetrating a tissue while a distal portion of an engagement catheter is suctionally engaged to a tissue, according to an exemplary embodiment of the present disclosure;

FIG. 35E shows a distal portion of a tension apparatus extending from a needle used to penetrate a tissue while a distal portion of an engagement catheter is suctionally engaged to a tissue, according to an exemplary embodiment of the present disclosure;

FIG. 35F shows a distal portion of a tension apparatus contacting a distal surface of a tissue while a distal portion of an engagement catheter is suctionally engaged to a proximal surface of the tissue, according to an exemplary embodiment of the present disclosure;

FIG. 35G shows a distal portion of a tension apparatus suctionally engaged to a distal surface of a tissue while a distal portion of an engagement catheter is suctionally engaged to a proximal surface of the tissue and while the tension apparatus is moved away from the engagement catheter so to gently stretch the tissue, according to an exemplary embodiment of the present disclosure; and FIG. 35H shows arms of a tension apparatus being folded toward one another to facilitate removal of the tension apparatus through the engagement catheter, according to an exemplary embodiment of the present disclosure.

Figure 1:
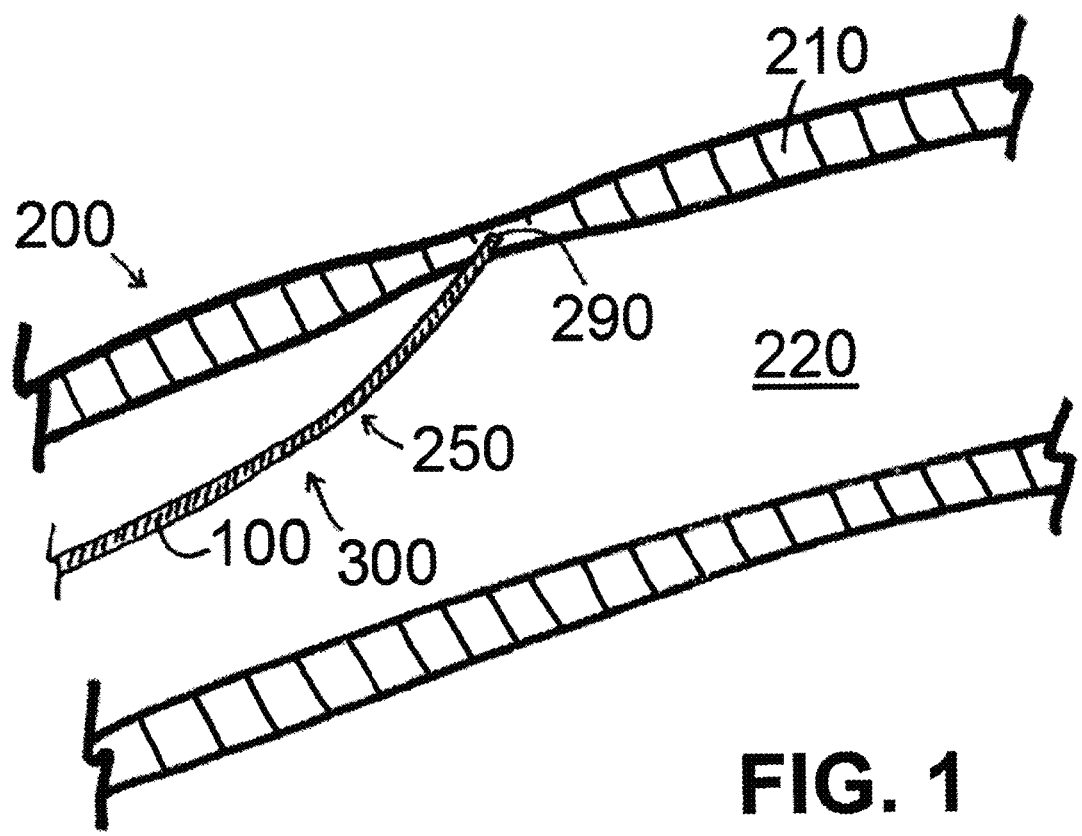
FIG. 1 shows a delivery mechanism delivering a material into a luminal organ wall via luminal or endothelial introduction/injection, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features, are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of various materials, and methods to administer the same, for injection into mammalian vessel or other luminal organ walls to provide additional support and/or integrity to the same.

In various embodiments of materials of the present disclosure, materials 100 or substances 1776 are non-degradable (or biodegradable, depending on application), non-inflammatory biopolymers. Exemplary materials 100 or substances 1776 within that scope included, but are not limited to, alginate, polytetrafluoroethylene (PTFE), elastomers (such as, for example, silicone elastomer, polyurethane, butyl rubber, and ethylene-propylene rubber, for example) and the like. Said materials 100 or substances 1776 are chosen so to provide a permanent or more permanent solution to the problems referenced herein, as said materials 100 or substances 1776 would last (not be biologically resorbed or otherwise broken down over time), would not introduce inflammation into the location of introduction, and are biocompatible. Additional materials 100 and/or substances 1776 of the present disclosure may include, but are not limited to, various drugs/medicaments, stem cells, other cells, etc., as used or developed in the art to treat a patient condition, for example. As said materials 100 or substances 1776 can be delivered via injection, as referenced in further detail herein, materials 100 or substances 1776 may be referred to as "liquid materials" in various embodiments, with the general understanding that said materials 100 would be injectable (such as a solution, a suspension, a gel, etc.), and may harden over time, as discussed in further detail herein.

Figure 2:
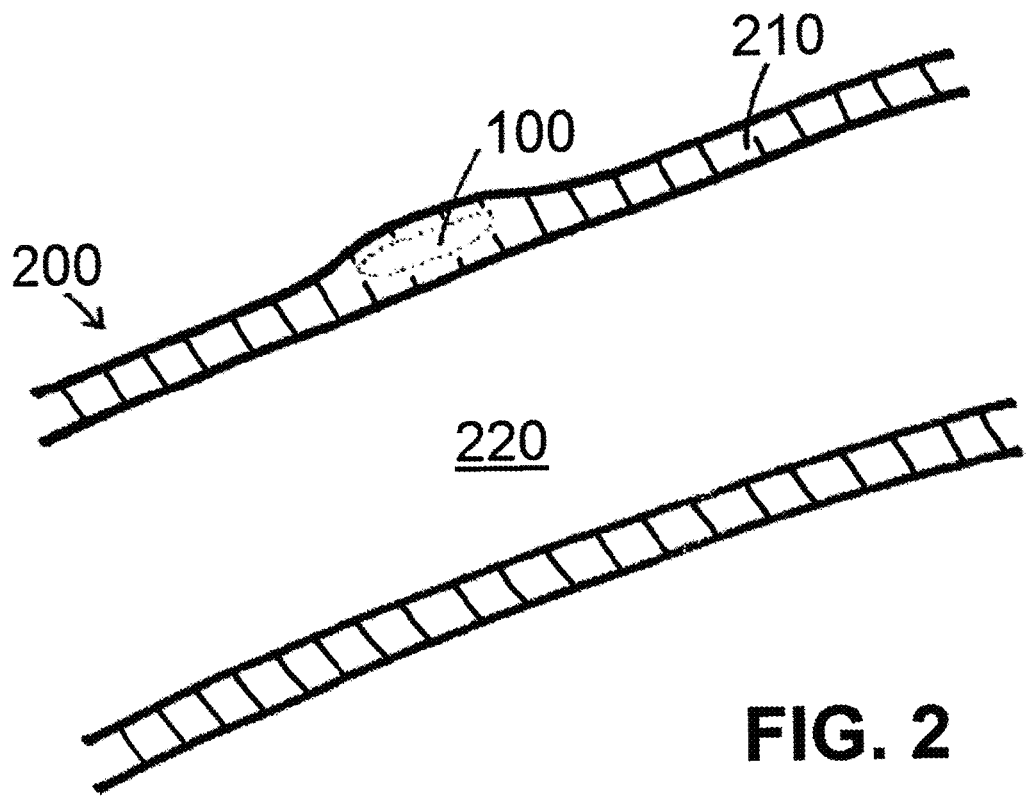
FIG. 2 shows material delivered into a luminal organ wall, according to an exemplary embodiment of the present disclosure.
Figure 3:
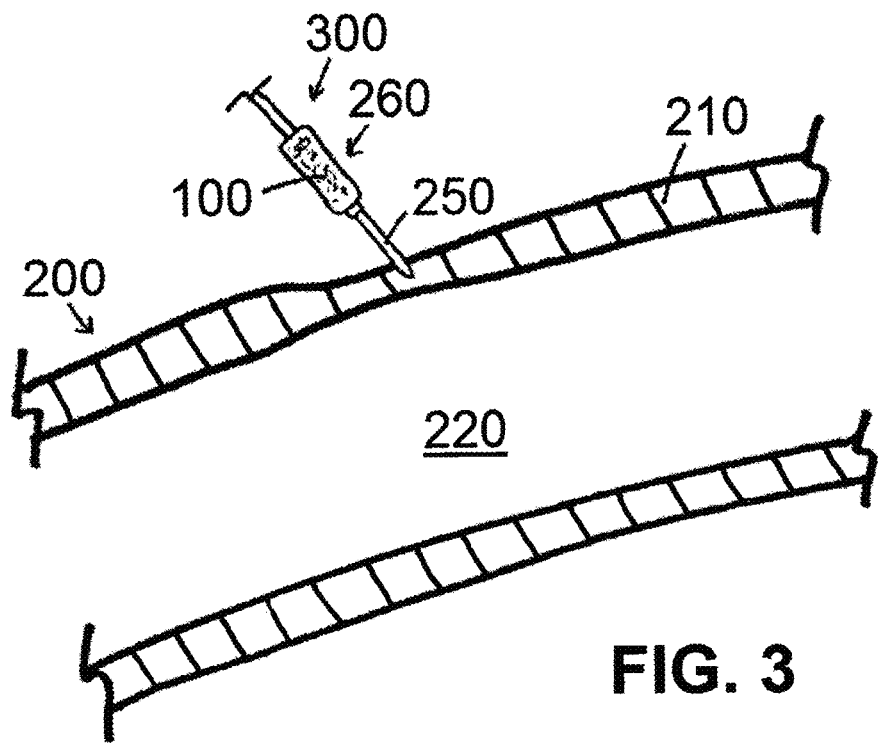
FIG. 3. shows a delivery mechanism delivering a material into a luminal organ wall via adventitial introduction/injection, according to an exemplary embodiment of the present disclosure.
Figure 4A:
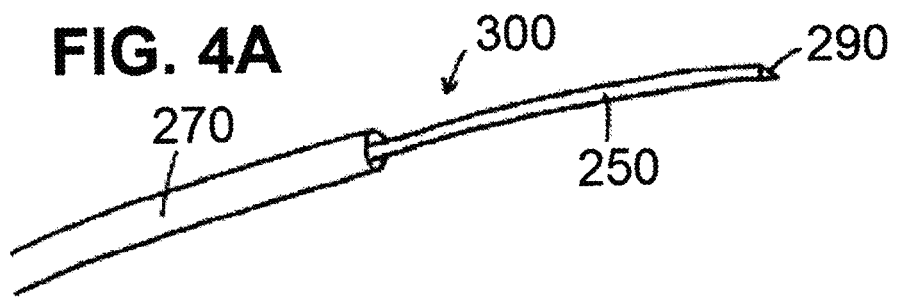
FIG. 4A shows a delivery mechanism configured as a needle within a catheter, according to an exemplary embodiment of the present disclosure.
Figure 4B:
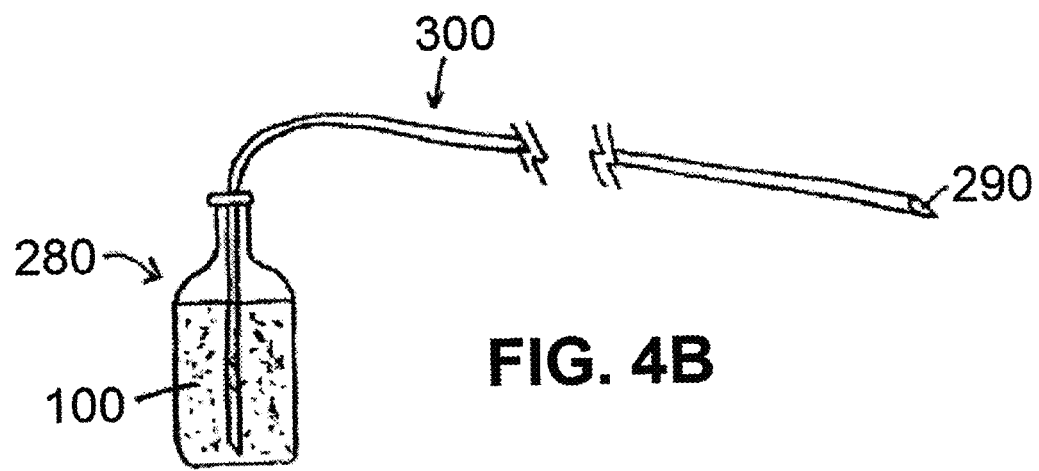
FIG. 4B shows a delivery mechanism configured as a needle in communication with a reservoir of material, according to an exemplary embodiment of the present disclosure.

Said materials 100 of the present disclosure can be introduced into a luminal organ wall 210 of a mammalian luminal organ 200, as shown in FIG. 2, so to, for example, increase a local and/or regional thickness of said luminal organ wall 210. Such an increase in thickness would then reduce luminal organ wall 210 stress, such as per LaPlace's law, so to prevent negative remodeling and/or potential rupture of luminal organ wall 210 at the location where materials 100 are introduced. In at least one embodiment/example, a first material 100, such as alginate and/or another polymeric material, can be positioned upon and/or injected into a mammalian luminal organ 200 or other non-luminal organ, as noted herein, and a second material 100, such as saline or another material 100 having a different ionic content than the first material 100, can subsequently be positioned upon and/or injected into a mammalian luminal organ 200 or other non-luminal organ. Such a procedure, for example, can be used to inject a liquid alginate (an exemplary material 100), and a second material 100, such as saline, can be injected so to cause the first material 100 to gel, harden, coagulate, etc., as may be desired, so to provide additional support upon and/or within mammalian luminal organ 200, such as by way of sodium ion exchange.

An exemplary introduction method of the present disclosure can be performed by way of injection, such as by using a needle 250 (alone, as part of a syringe 260, connected to or within a catheter 270, etc.) or other injection device known or developed in the medical arts to inject a material into a tissue. Such an injection can be made from within a lumen 220 of a mammalian luminal organ 200, referred to as luminal or endothelial introduction/injection, or from the outside of mammalian luminal organ 200, referred to as adventitial introduction/injection, by way of introducing material 100 from a material source 280 (which may be a reservoir containing material 100, such as a syringe 260 or other reservoir) through needle 250, out of needle aperture 290 (such as at a relative distal end of needle 250) into luminal organ wall 210. Various needles 250 or 1890, syringes 260, and/or catheters 270, etc., may be generally referred to herein as delivery mechanism(s) 300.

In various embodiments, for example, mammalian luminal organs 200 may comprise blood vessels, a thinned esophagus, a thin bladder, or another vessel or luminal organ within the mammalian body. In the case of a blood vessel as mammalian luminal organ 200, an aorta (relating to an aneurysm within a thin aorta wall), a thin cerebral vessel (relating to cerebral aneurysms), and the like, materials 100 of the present disclosure can be introduced into the luminal organ wall 210 of said mammalian luminal organs 200 so to improve the overall internal structural integrity of the same, reduce stress, and reduce or eliminate the risk of rupture, which can be fatal. In the case of a thin esophagus (achalasia) as mammalian luminal organ 200, such as in achalasia, materials 100 of the present disclosure can be introduced into the luminal organ wall 210 of said mammalian luminal organs 200 so to improve the overall internal structural integrity of the same, reduce stress, and improve the overall comfort level and health of the patient receiving the materials 100. The same can be said for a thin bladder as mammalian luminal organ 200, as materials 100, when introduced into luminal organ wall 210 of the same so to improve the structural integrity of the same. In view of the foregoing, various materials 100 of the present disclosure can be used to treat the aforementioned conditions/diseases.

Figure 5:
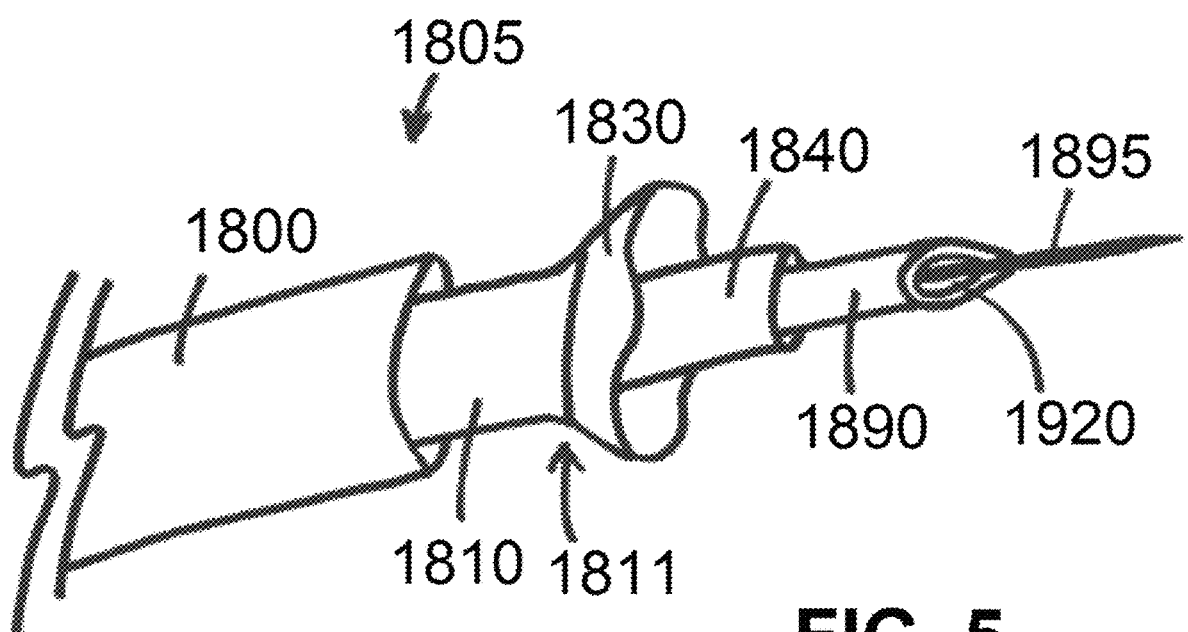
FIG. 5 shows a distal portion of system for isolating tissue and/or delivering a material, according to an exemplary embodiment of the present disclosure.

An exemplary system for isolating tissue and/or delivering a material 100 of the present disclosure is shown in FIG. 5. As shown in FIG. 5, distal portion of an exemplary system 1805 (which may also be referred to as a delivery mechanism 300) may comprise an engagement catheter 1810 having a skirt or suction cup 1830 at or near a distal end 1811 of engagement catheter 1810. System 1805 may further comprise a sleeve 1800 positioned around portions of engagement catheter 1810 and configured for sliding movement relative to engagement catheter 1810 such that movement of sleeve 1800 relative to engagement catheter 1810 can cause skirt or suction cup 1830 to be within or external to sleeve 1800. System 1805 may further comprise a delivery catheter 1840 (which may also be referred to as catheter 270) configured to fit within engagement catheter 1810 and configured for sliding movement relative to engagement catheter 1810. System 1805 may further comprise a needle 1890 (which may also be referred to as needle 250) defining a needle aperture 1920 (which may also be referred to as needle aperture 290) and configured to fit within delivery catheter 1840 and/or engagement catheter 1810 and configured for sliding movement relative to delivery catheter 1840 and/or engagement catheter 1810. System 1805 may further comprise a wire 1895 configured to fit within engagement catheter 1810, delivery catheter 1840, and/or needle 1890, and configured for sliding movement relative to engagement catheter 1810, delivery catheter 1840, and/or needle 1890. Components of such exemplary system 1805 embodiments may be as described within U.S. Pat. No. 8,328,752 of Kassab et al., the contents of which are expressly incorporated herein by reference.

Figure 6:
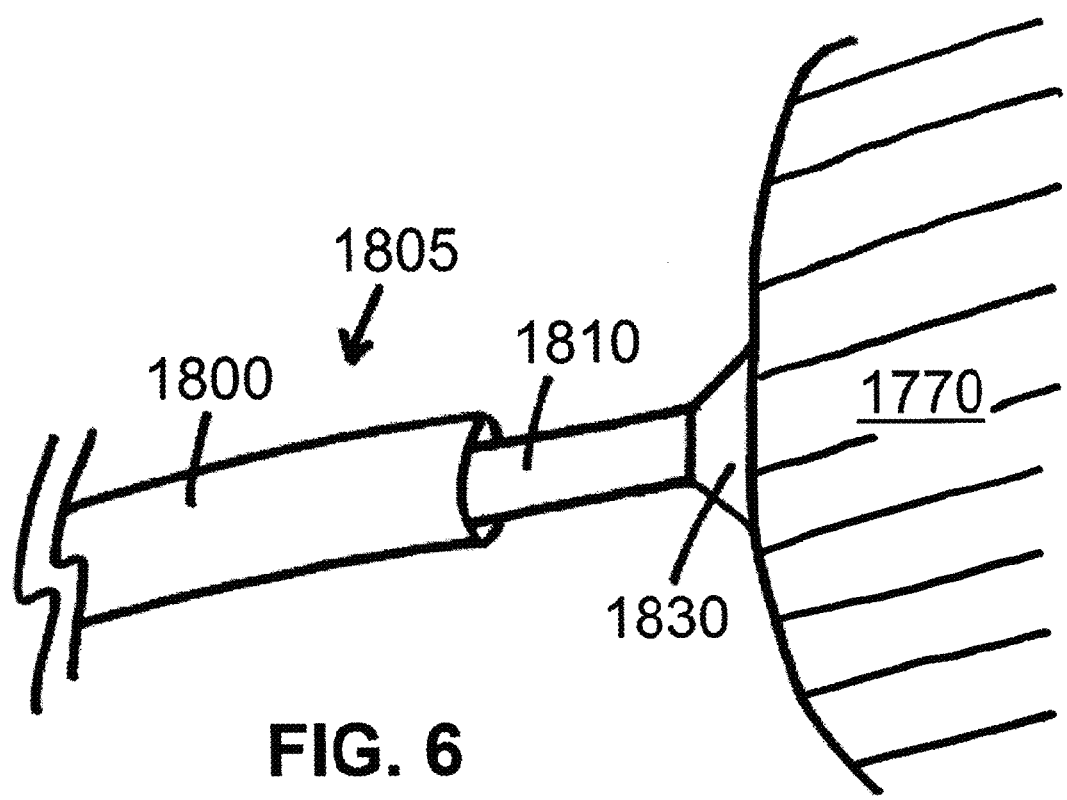
FIG. 6 shows a distal portion of a system suctionally affixed to a mammalian tissue, according to an exemplary embodiment of the present disclosure.

FIG. 6 shows a distal portion of an exemplary system 1805 of the present disclosure, with system 1805 comprising a sleeve 1800 positioned at least partially around engagement catheter 1810 having a skirt or suction cup 1830 at or near a distal end 1811 of engagement catheter 1810. Skirt or suction cup 1830 is shown as engaging cardiac tissue 1770, such as a myocardium, a left ventricle, or other portions of cardiac tissue 1770 or other mammalian tissue. Such engagement is provided via suction through engagement catheter 1810. Suction can be provided as described within U.S. Pat. No. 8,328,752 of Kassab et al., noting that various portions of devices and/or systems disclosed within U.S. Pat. No. 8,328,752 of Kassab et al. may be used in connection with devices and/or systems of the present disclosure.

Procedurally, portions of delivery mechanisms 300 and/or systems 1805 can be delivered subendocardially, such as by way of needle puncture, so that skirt or suction cup 1830 is ultimately positioned against cardiac tissue 1770 (or other mammalian tissues) as desired. Various delivery mechanisms 300 and/or portions of systems 1805 of the present disclosure can be delivered intravascularly, via thoracic puncture, etc., for ultimate use within the body, or can be used external to the body, such as upon the skin.

Figure 7:
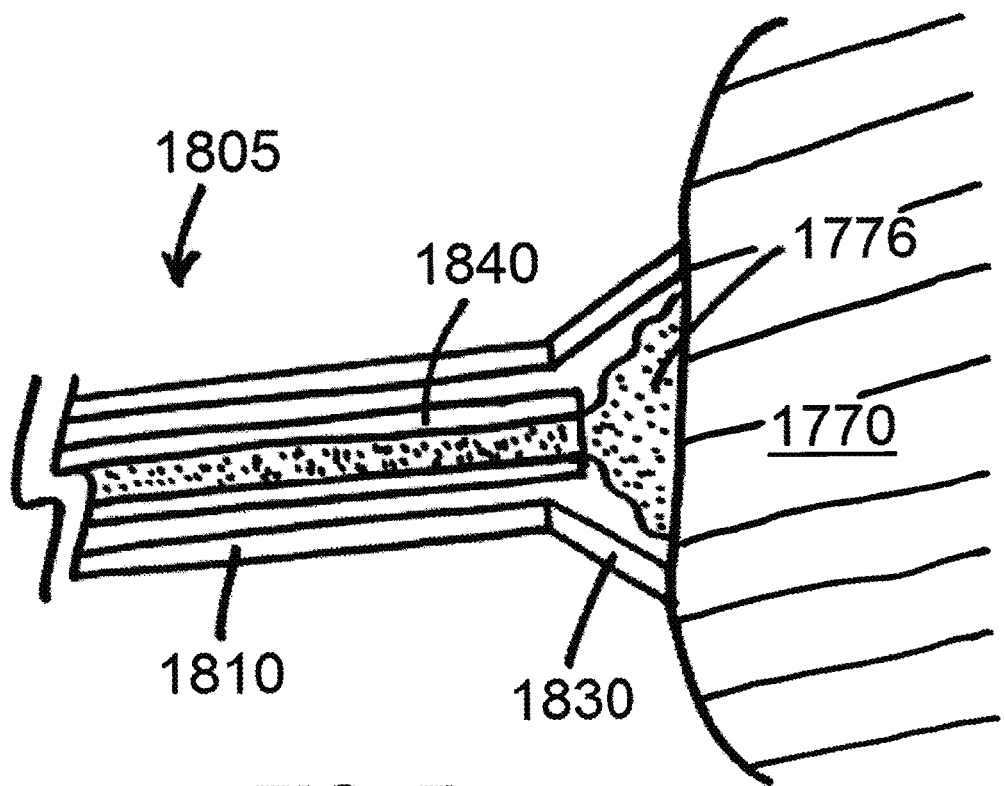
FIG. 7 shows a cut-away view of a distal portion of a system suctionally affixed to a mammalian tissue with a liquid material positioned therein, according to an exemplary embodiment of the present disclosure.
Figure 8:
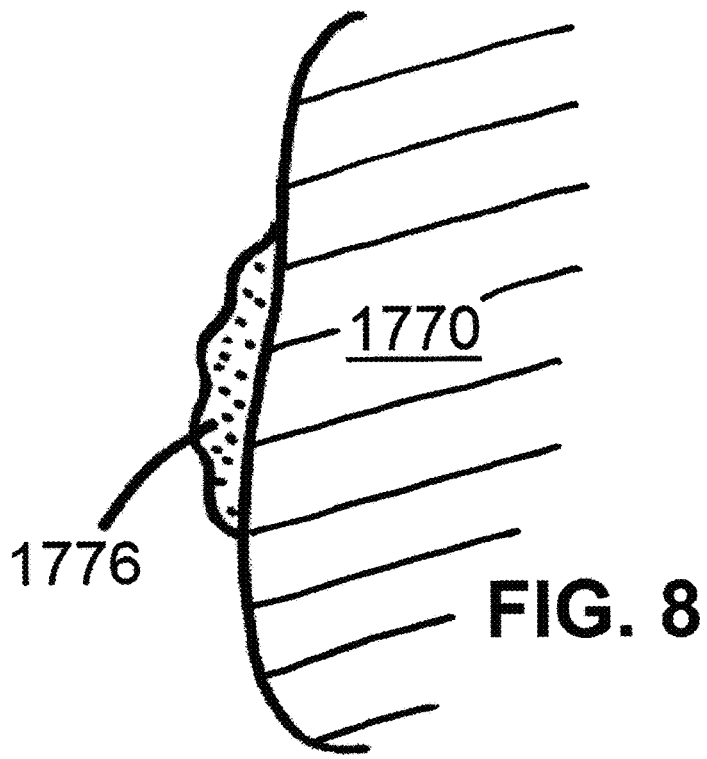
FIG. 8 shows a quantity of coagulated liquid material adhered to a mammalian tissue, according to an exemplary embodiment of the present disclosure.
Figure 9:
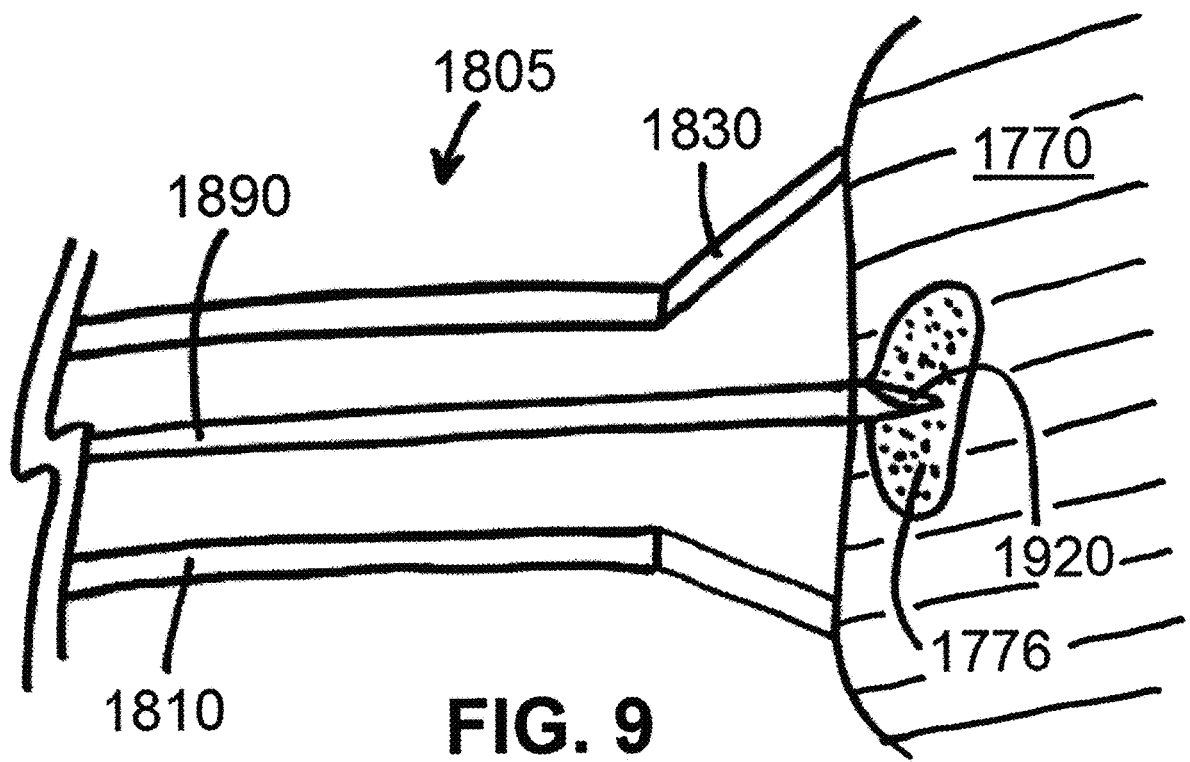
FIG. 9 shows a cut-away view of a distal portion of a system suctionally affixed to a mammalian tissue, according to an exemplary embodiment of the present disclosure.

FIG. 7 shows the injection of a substance 1776 (which can also be (or be referred to as) a material 100) through delivery catheter 1840 while skirt or suction cup 1830 of engagement catheter 1810 is suctionally engaged to cardiac tissue 1770. Substance 1776 can be injected through delivery catheter 1840, such as shown in FIG. 7, or delivered through needle 1890, such as shown in FIG. 9. Substance 1776 can congeal, coagulate, harden, and/or generally exist on a surface of a tissue (such as cardiac tissue 1770), such as shown in FIGS. 7 and 8, or within the tissue wall itself, such as shown in FIG. 9.

Figure 10:
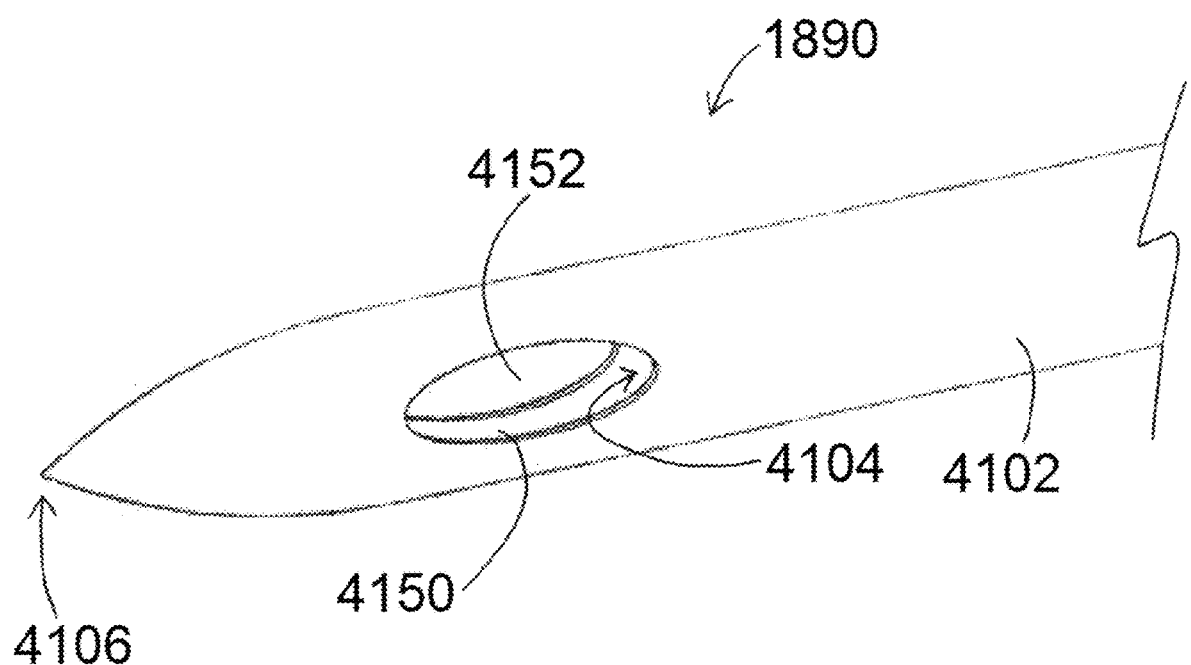

An exemplary embodiment of a portion of a needle of the present disclosure is shown in FIG. 10. As shown in FIG. 10, an exemplary needle 1890 (distal portion shown in the figure) comprises an elongated body 4102, which can be generally cylindrical in shape for at least part of an overall length of needle 1890, with elongated body 4102 defining a lumen 4104 extending along at least part of an overall length of needle 1890. Needle 1890, as shown in FIG. 10, terminates at a pointed tip 4106, with the size and shape of pointed tip 4106 permitting pointed tip 4106 to puncture a tissue or organ, such as the skin and/or a wall of a luminal organ, such as a heart wall.

Needle 1890, as shown in FIG. 10, has a first distal aperture 4150 and a second distal aperture 4152 defined therein near a distal portion of needle 1890 along a relative sidewall of elongated body 4102. First distal aperture 4150 and second distal aperture 4152 are defined within elongated body 4102 so that, for example, contents within lumen 4104 of needle 1890 can be injected out of needle 1890 via first distal aperture 4150 and/or second distal aperture 4152. First distal aperture 4150 and/or second distal aperture 4152 can each have various shapes, such as an oval shape (as shown in FIG. 10), a round shape, a square shape, and/or various other shapes. First distal aperture 4150 and second distal aperture 4152 may be defined within elongated body 4102 on opposite relative sides of elongated body 4102, such as shown in FIG. 10, or closer to one another (not directly opposite one another). As shown in FIG. 10, first distal aperture 4150 and second distal aperture 4152, in an exemplary embodiment, are not located at pointed tip 4106, but proximal to pointed tip 4106, so that first distal aperture 4150 and second distal aperture 4152 are along relative "sides" of elongated body 4102. Using such a needle 1890 embodiment, infusion of a material 100 or substance 1776 through said needle 1890 would be through the relative "side ports" (first distal aperture 4150 and second distal aperture 4152), noting that said side ports could be positioned at any location along a length of needle 1890, but having said side ports closest to pointed tip 4106 without impinging on needle 1890 curvature, for example, would reduce the required puncture depth, and therefore reduce the risk of potential perforation.

Figure 11:
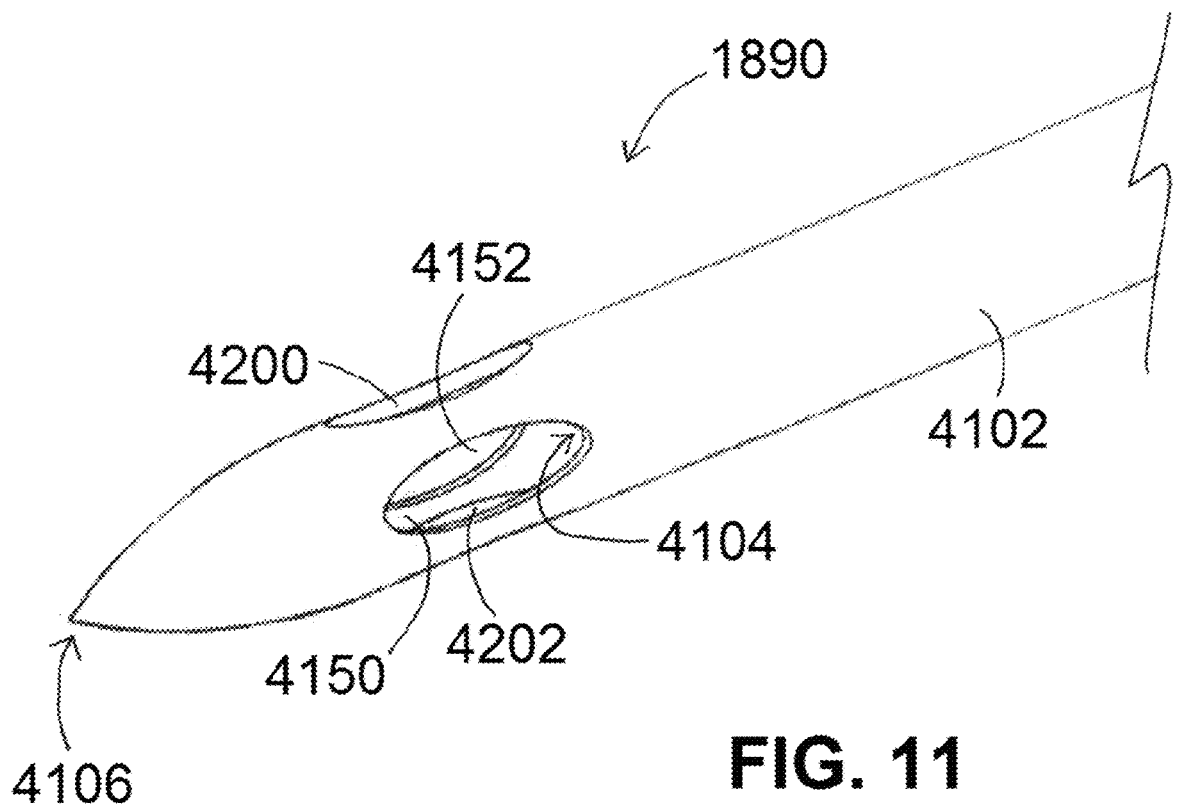

Another exemplary embodiment of a portion of a needle of the present disclosure is shown in FIG. 11. Needle 1890, as shown in FIG. 11, has a first distal aperture 4150, a second distal aperture 4152, a third distal aperture 4200, and a fourth distal aperture 4202 defined therein near a distal portion of needle 1890 along a relative sidewall of elongated body 4102. First distal aperture 4150, second distal aperture 4152, third distal aperture 4200, and fourth distal aperture 4202 are defined within elongated body 4102 so that, for example, contents within lumen 4104 of needle 1890 can be injected out of needle 1890 via first distal aperture 4150, second distal aperture 4152, third distal aperture 4200, and/or fourth distal aperture 4202. First distal aperture 4150, second distal aperture 4152, third distal aperture 4200, and fourth distal aperture 4202 can each have various shapes, such as an oval shape (as shown in FIG. 11), a round shape, a square shape, and/or various other shapes. First distal aperture 4150, second distal aperture 4152, third distal aperture 4200, and fourth distal aperture 4202 may be defined within elongated body 4102 so that they are equidistant from one another, such as shown in FIG. 11, or in a different arrangement, as may be desired. As shown in FIG. 11, first distal aperture 4150, second distal aperture 4152, third distal aperture 4200, and fourth distal aperture 4202, in an exemplary embodiment, are not located at pointed tip 4106, but proximal to pointed tip 4106, so that first distal aperture 4150, second distal aperture 4152, third distal aperture 4200, and fourth distal aperture 4202 are along relative "sides" of elongated body 4102. Such an embodiment would allow, for example, full radial infusion of material 100 or substance 1776 from needle 1890.

Various needle 1890 embodiments of the present disclosure can have various numbers of distal apertures (such as first distal aperture 4150, second distal aperture 4152, third distal aperture 4200, and/or fourth distal aperture 4202) defined along a relative sidewall of elongated body, such as two (as shown in FIG. 10), three, four (as shown in FIG. 11), five, or more distal apertures.

Figure 12:
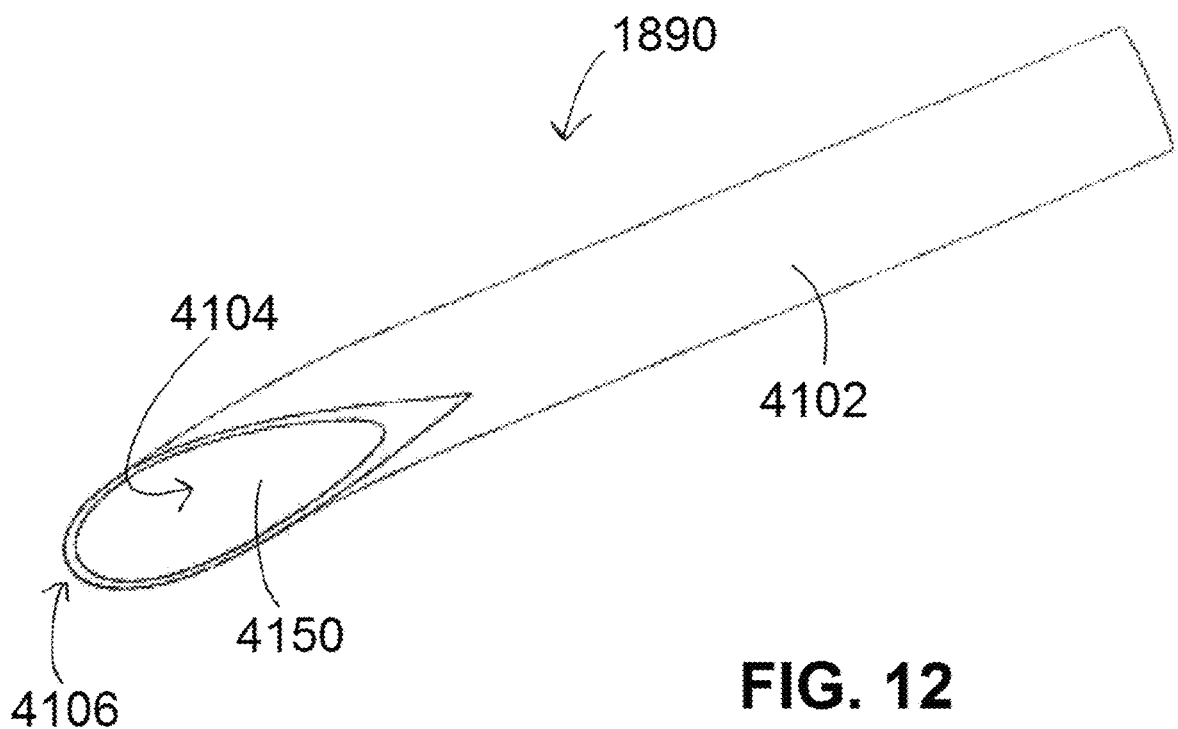

Another exemplary embodiment of a portion of a needle of the present disclosure is shown in FIGS. 12 and 13. Needle 1890, as shown in FIGS. 12 and 13, comprises an elongated body and a first distal aperture 4150 (which may also be referred to as needle aperture 1920, as referenced herein) defined within elongated body 4102 at pointed tip 4106 so that first distal aperture 4150 extends proximally from pointed tip 4106 at a distal end of needle 1890. First distal aperture 4150 can be relatively round and/or curved at a distal portion, and taper inward toward a proximal portion of first distal aperture 4150, such as shown in FIG. 12, for example. First distal aperture 4150, such as shown in FIG. 13, is "open" on a relative "side" of elongated body 4102, so that a substance present within lumen 4104 can exit first distal aperture 4150, such as when needle 1890 is used for injection, so that substance is directed out of needle 1890 in a direction that is not the direction of the axis defined by elongated body 4102, such as shown in FIG. 13 via X-X'. Such an embodiment would allow for orthogonal injection at a deepest point of insertion, as described in further detail herein.

Prior art needles, as shown in the side view and perspective views shown in FIG. 14 for example, generally include a distal aperture that is angled from one relative "side" of the needle to the other, such that the distal aperture is angled as shown in the upper part of said figure. Needle 1890 shown in FIGS. 12 and 13, for example, differ from the needles shown in FIG. 14 in that needles 1890 shown in FIGS. 12 and 13 define a first distal aperture 4150 having an opening that is generally parallel with the axis defined by elongated body 4102, such as shown in FIG. 13 via X-X'. Substances discharged from the distal aperture in the needle shown in FIG. 14 would be discharged in a direction defined by the axis shown via X-X' therein, while substances injected through any of needles 1890 shown in FIGS. 10-13 would not be discharged in a direction defined by the axis shown via X-X' in FIG. 13, as said substances would be discharged in a direction other than that defined by said axis.

Various needles 1890 of the present disclosure can be used alone, or in conjunction with other devices, to deliver a substance to a targeted tissue as may be desired. One such delivery process is the process of delivering a substance subendocardially along with suction, as follows.

Figure 15:
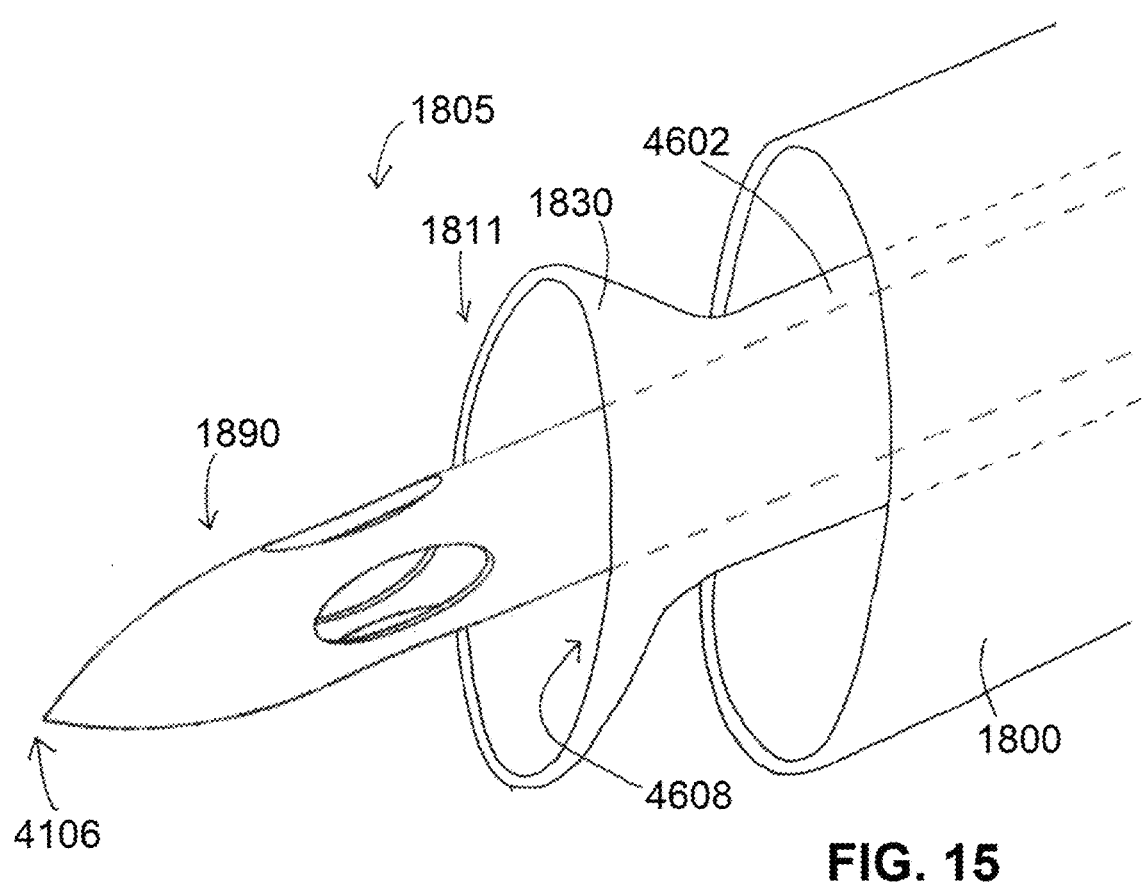
FIG. 15 shows a distal portion of system for isolating tissue and/or delivering a material, according to an exemplary embodiment of the present disclosure.

FIG. 15 shows portions of an exemplary system 1805 of the present disclosure. As shown in FIG. 15, an exemplary system 1805 of the present disclosure comprises a needle 1890 of the present disclosure and a suction catheter 4602 (which may also be referred to herein as an engagement catheter 1810) having a skirt or suction cup 1830 located at a distal end 1811 of suction catheter 4602. Needle 1890 can be delivered through a lumen 4608 defined within suction catheter 4602, such as shown in FIG. 15, and an optional sleeve 1800 can be positioned around at least part of suction catheter 4602. Procedurally, a guide wire (not shown) can be delivered through the skin, into an artery (such as the femoral artery or another artery of interest), and a distal end of the guide wire can be advanced intravascularly until it is positioned at a location of interest, such as inside a left ventricle of the heart. Needle 1890, catheter 4602, sleeve 1800, and/or a combination of two or more of the foregoing, can be advanced along the guidewire so that ultimately the distal end of needle 1890 and the distal end 1811 of suction catheter 4602 are positioned at or near a tissue of interest, such as the free wall (or the subendocardium or the subendocardial wall) of the left ventricle. Skirt or suction cup 1830 can be positioned against the tissue of interest, and suction through suction catheter 4602 can cause skirt or suction cup 1830 to suctionally adhere to said tissue. Pointed tip 4106 of needle 1890 can be advanced into the tissue of interest before suction is applied via suction catheter 4602, at the same time suction is started through suction catheter 4602, or after suction is started through suction catheter 4602, as may be desired. After the various distal apertures (such as distal apertures 4150, 4152, 4200, and/or 4202, for example) are located within the tissue of interest or are located within a luminal organ of interest, a substance can be delivered through lumen 4104 of needle and out of said apertures 4150, 4152, 4200, and/or 4202, for example. In at least one embodiment, needle 1890 is advanced into a free wall of a left ventricle of a heart so that apertures 4150, 4152, 4200, and/or 4202, for example are located within said free wall, and a substance, such as a substance used to strengthen a tissue wall, is injected into the tissue wall. Skirt or suction cup 1830, at a distal end of suction catheter 4602, has a larger distal perimeter or circumference than the perimeter or circumference of the remainder of suction catheter 4602 (or at least the elongated portion of suction catheter 4602) so to allow for a larger suction area against the tissue or organ of interest.

Delivery mechanisms 300 and/or systems 1805 can be used as follows, by way of example:

a) to suctionally engage a mammalian tissue or organ so to stabilize said tissue or organ; and/or b) to suctionally engage a tissue or organ so to directly deliver a medicament, such as a pharmaceutical compound (a drug), an injectable material (such as a biopolymer), a lead, cells, a coil, and/or another medical device; and/or c) to suctionally engage a tissue or organ so to facilitate delivery of a delivery catheter 1840, a needle 1895, and/or a wire 1920 through delivery mechanism 300, whereby said delivery catheter 1840 and/or needle 1895 can be used to deliver a medicament, such as a pharmaceutical compound, an injectable material, a lead, a coil, and/or another medical device, and/or whereby wire 1920 can be used to guide portions of delivery mechanism 300 and/or system 1805 within the body.

Figure 16:
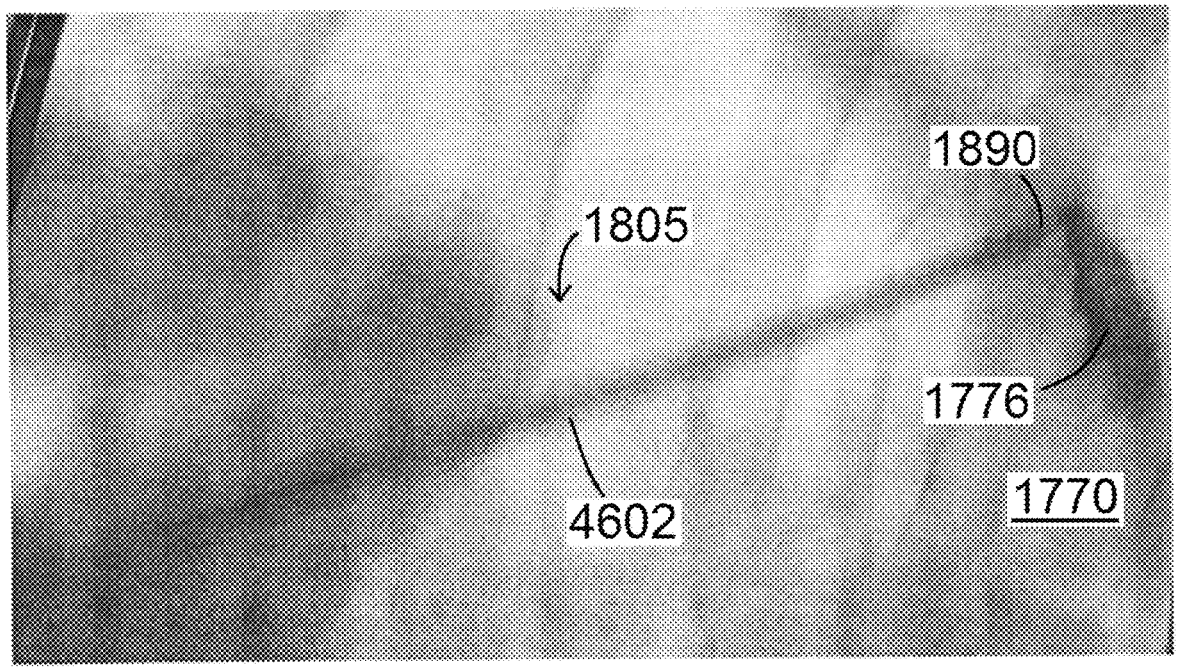
FIG. 16 shows a photograph of injection of a substance using a needle while under suction via a suction catheter, according to an exemplary embodiment of the present disclosure.
Figure 17:
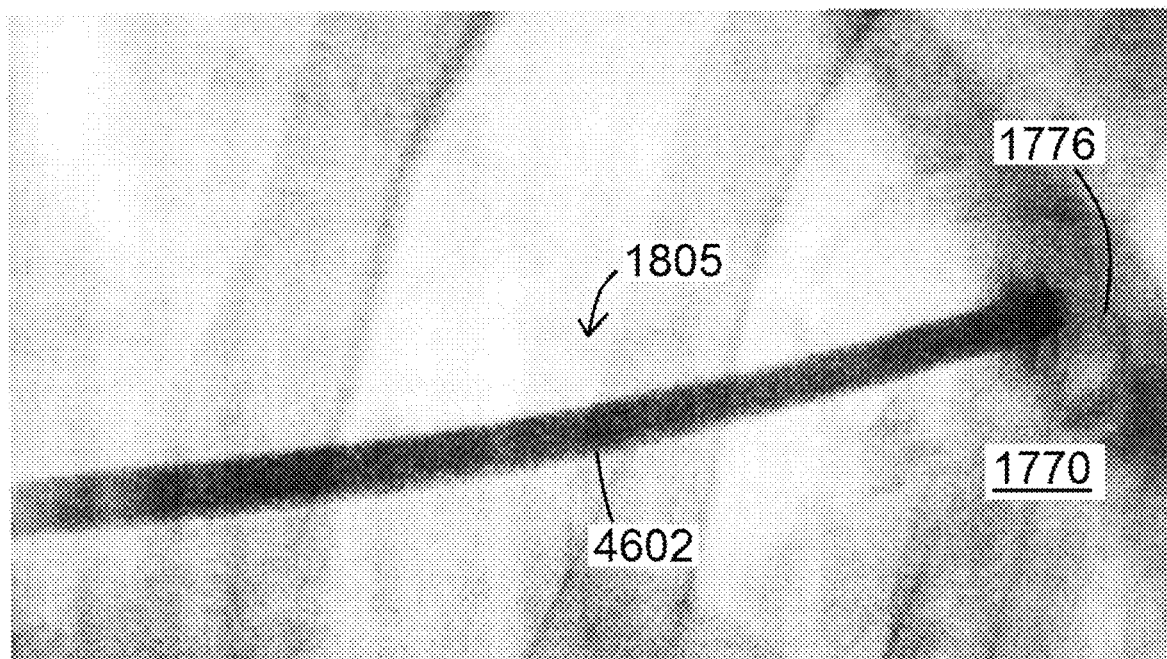
FIG. 17 shows a photograph of a suction catheter suctionally engaging a tissue after injection of the substance, according to an exemplary embodiment of the present disclosure.
Figure 18:
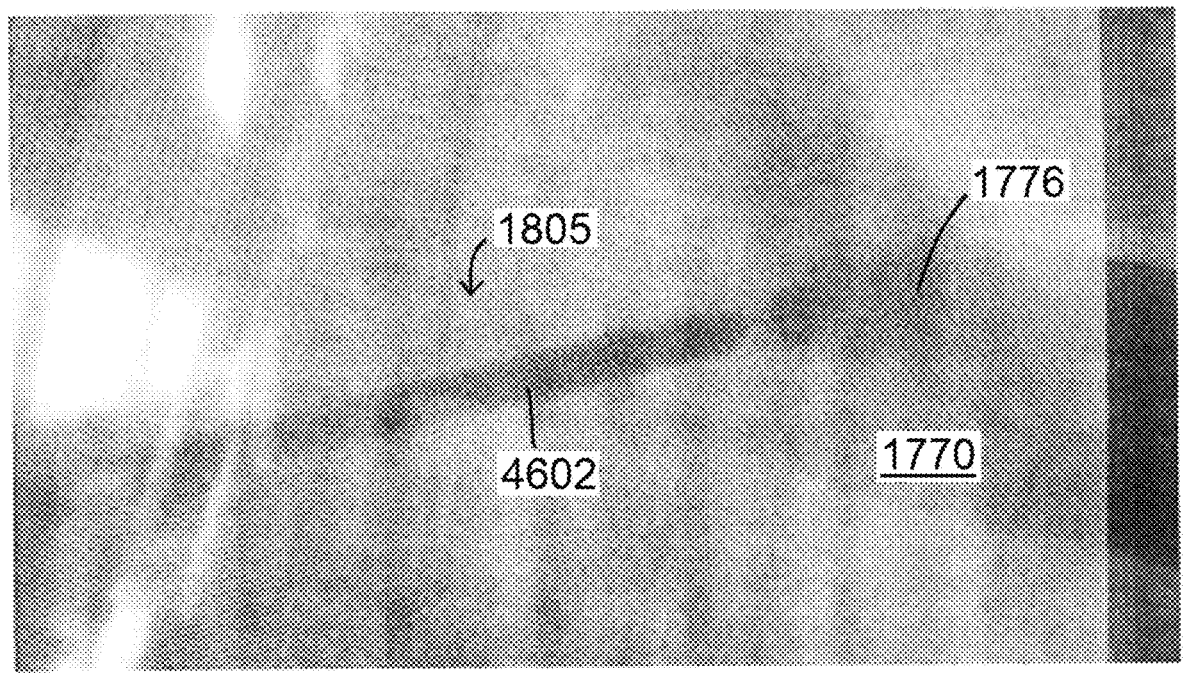
FIG. 18 shows a photograph of a suction catheter disengaged from a tissue after injection of the substance, according to an exemplary embodiment of the present disclosure.

In at least one embodiment of using a delivery mechanism and/or system 1805 of the present disclosure, said delivery mechanism 300 and/or system 1805 is used as follows, noting that all steps are not required, but may be performed:

i) after puncturing the skin to provide access to an artery of interest, advancing a wire 1895 so that a distal end of wire 1895 is positioned at a desired location within the body, such as within a left ventricle of a heart, by way of the femoral artery to the aorta to the left ventricle, for example;

ii) advancing other portions of delivery mechanisms 300 and/or systems 1805 over said wire 1895, such as an engagement catheter 1810 or suction catheter 4602, needle 1890, sleeve 1800, etc, so that distal portions of each are located at, near, or within the left ventricle of the heart;

iii) applying suction through engagement catheter 1810 or suction catheter 4602 so that skirt or suction cup 1830 of engagement catheter 1810 or suction catheter 4602 can suctionally engage a tissue of interest, such as the free wall of the left ventricle;

iv) inserting a distal end of needle 1890 into the tissue of interest, such as the free wall of the left ventricle, and injecting a material 100 or substance 1776 into said tissue (such as into the free wall of the left ventricle), such as to inject a biopolymer into the free wall itself to support the free wall, all while suction is applied through engagement catheter 1810 or suction catheter 4602, such as shown in FIG. 16, for example;

v) withdrawing needle 1890 from said tissue, while suction is applied through engagement catheter 1810 or suction catheter 4602, so that any material 100 or substance 1776 that may leak from the needle puncture location of said tissue would be removed from the left ventricle via suction through engagement catheter 1810 or suction catheter 4602, such as shown in FIG. 17, for example; and vi) after a desired amount of time has elapsed, ceasing suction through engagement catheter 1810 or suction 4602 so to disengage from the tissue of interest, such as cardiac tissue 1770, such as shown in FIG. 18, for example.

Needle 1890 design, such as shown in FIGS. 10-13 and referenced herein, allows for material 100 or substance 1776 to be injected at an angle other than 0° relative to the elongated axis of needle 1890, as referenced herein. Such a relative sideways or angled injection may allow material 100 and/or substance 1776 to better remain within the tissue of interest and potentially reduce the leakage from the tissue of interest when needle 1890 is removed therefrom.

Re: step iv) above, needle 1890 may be positioned within the tissue for a desired period of time, such as one minute, two minutes, or longer or shorter as may be desired, to allow material 100 or substance 1776 to harden, congeal, etc., and therefore reduce potential leakage from said tissue. One notable risk of leakage is the potential embolization of said material 100 or substance 1776, which could be fatal (potentially) should it be released within the bloodstream. Such a method, by way of using suction during and after the injection procedure, would remove any potential leaked material 100 or substance 1776 from the bloodstream.

Said methods, for example, could be performed to treat a cardiac condition of a patient, such as a patient with a weakened left ventricle wall, by supporting/strengthening said left ventricle wall using an injected biopolymer. Such a treatment would be performed endovascularly instead of requiring open chest surgery, for example, resulting in less trauma to the patient, a lower infection risk, and likely less cost to perform the procedure.

Figure 19:
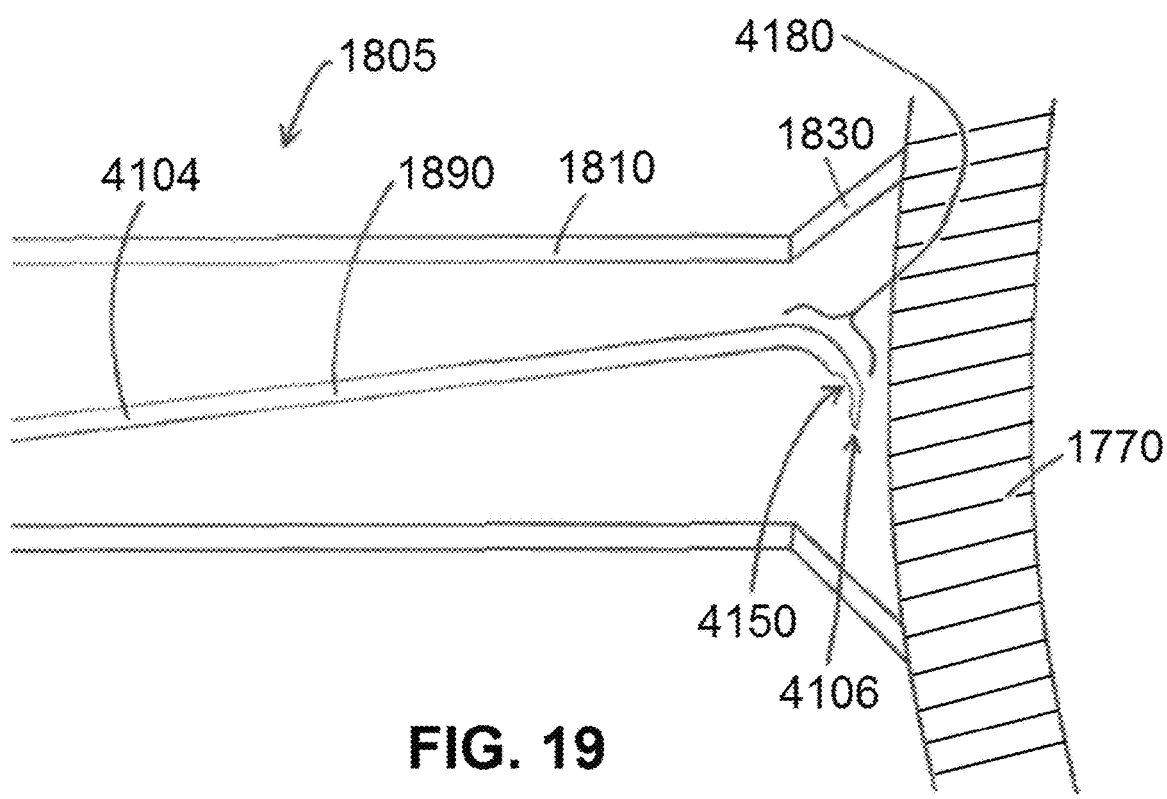
FIG. 19 shows a cut-away view of a distal portion of a system suctionally affixed to a mammalian tissue via an engagement catheter, according to an exemplary embodiment of the present disclosure.

FIGS. 19-24 show an embodiment of devices and systems used to perform such a method. For example, FIG. 19 shows a distal portion of an exemplary system 1085 comprising at least an engagement catheter 1810 having a skirt or suction cup 1830 at its distal end, and a needle 4150 having a curved distal portion 4180, in an exemplary embodiment. Suction can be applied through engagement catheter 1810, as shown in FIGS. 19-24, so to suctionally attach skirt or suction cup 1830 to cardiac tissue 1770 or other mammalian tissue.

Figure 20:
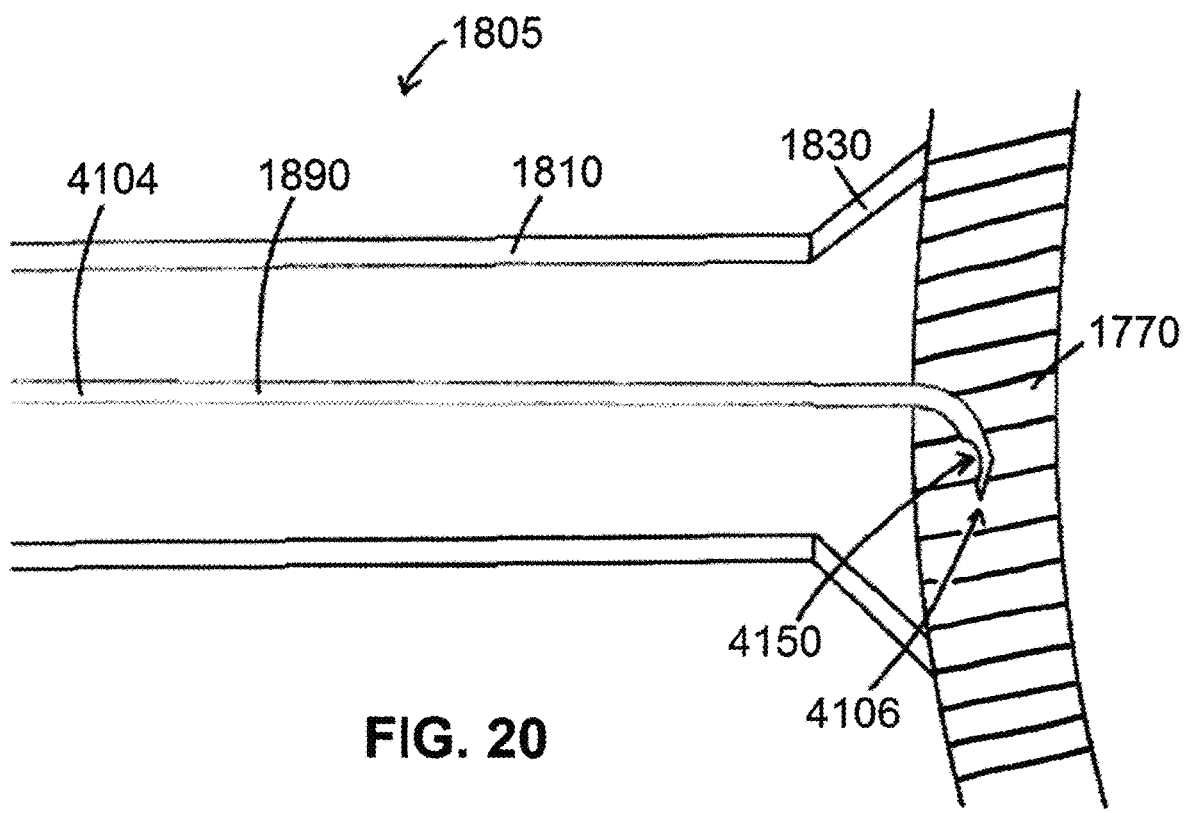
FIG. 20 shows a cut-away view of a distal portion of a system suctionally affixed to a mammalian tissue and whereby a needle has punctured a tissue of interest, according to an exemplary embodiment of the present disclosure.
Figure 21:
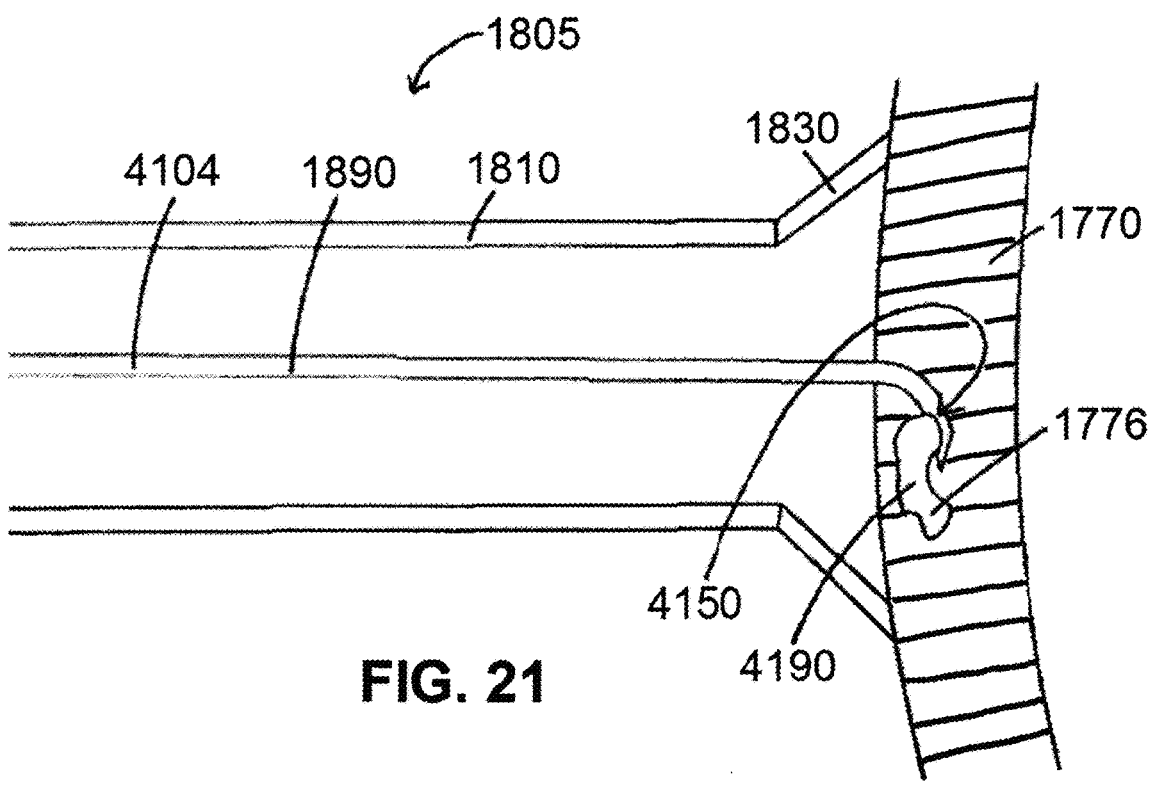
FIG. 21 shows a cut-away view of a distal portion of a system suctionally affixed to a mammalian tissue and whereby a needle has injected a bolus of a substance into the tissue of interest, according to an exemplary embodiment of the present disclosure.

FIG. 20 shows needle 1890, whereby pointed tip 4106 of needle 1890 was used to puncture tissue 1770. FIG. 21 shows needle 1890 being used to inject a substance 1776, through lumen 4104 of needle 1890 and out of first distal aperture 4150 (and/or any other distal apertures of the present disclosure) into tissue 1776, forming a bolus 4190 of substance 1776 within tissue. Such an injection can also be performed while under suction within engagement catheter 1890.

In various embodiments, such as shown in FIGS. 19-22, first distal aperture 4150 (and/or any other distal apertures of the present disclosure) are relatively elongated, such as comprising a general oval or ovular shape, for example, so to generate a bolus 4190 having a geometry that is less likely to leak out of tissue 1770 upon removal of needle 1890 therefrom. Due to one or more characteristics of needle 1890, such as, for example, an elongated first distal aperture aperture 4150 (and/or any other distal apertures of the present disclosure), and/or a plurality of distal apertures as referenced herein, and/or a curved distal portion 4180 of needle 1890, for example, a bolus 4190 of substance 1770 is less likely to leak from tissue 1770 upon removal of needle 1890 therefrom as compared to using a prior art needle, as there would be a direct/straight path for potential bolus 4190 leakage using a prior art needle as compared to needles 1890 of the present disclosure.

Figure 22:
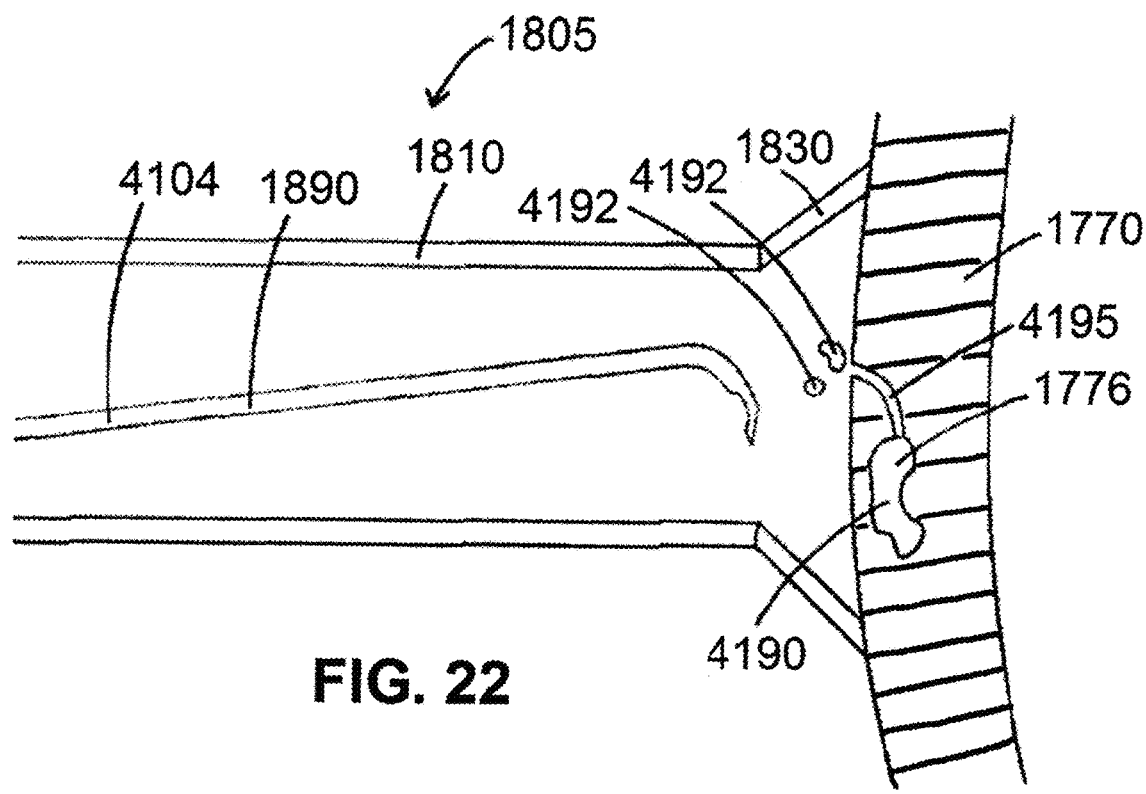
FIG. 22 shows a cut-away view of a distal portion of a system suctionally affixed to a mammalian tissue and after the needle has injected a bolus of a substance into the tissue of interest, according to an exemplary embodiment of the present disclosure.
Figure 23:
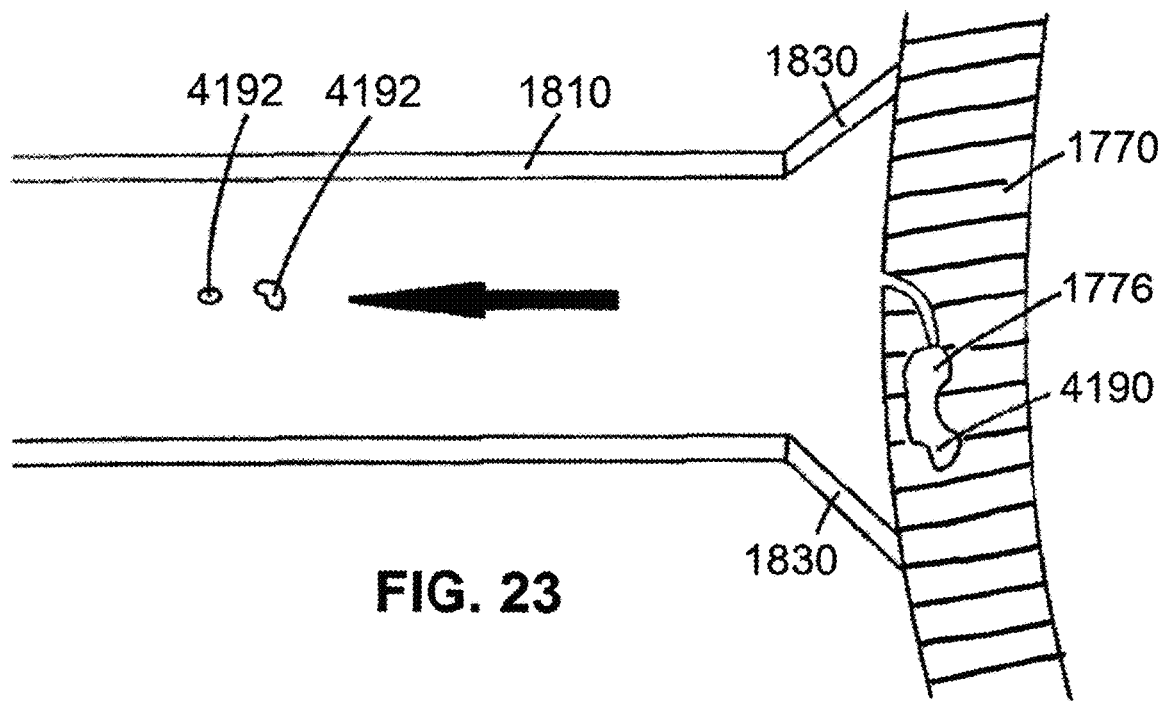
FIG. 23 shows a cut-away view of a distal portion of a system suctionally affixed to a mammalian tissue and used to remove escaped substance using suction within the engagement catheter, according to an exemplary embodiment of the present disclosure.
Figure 24:
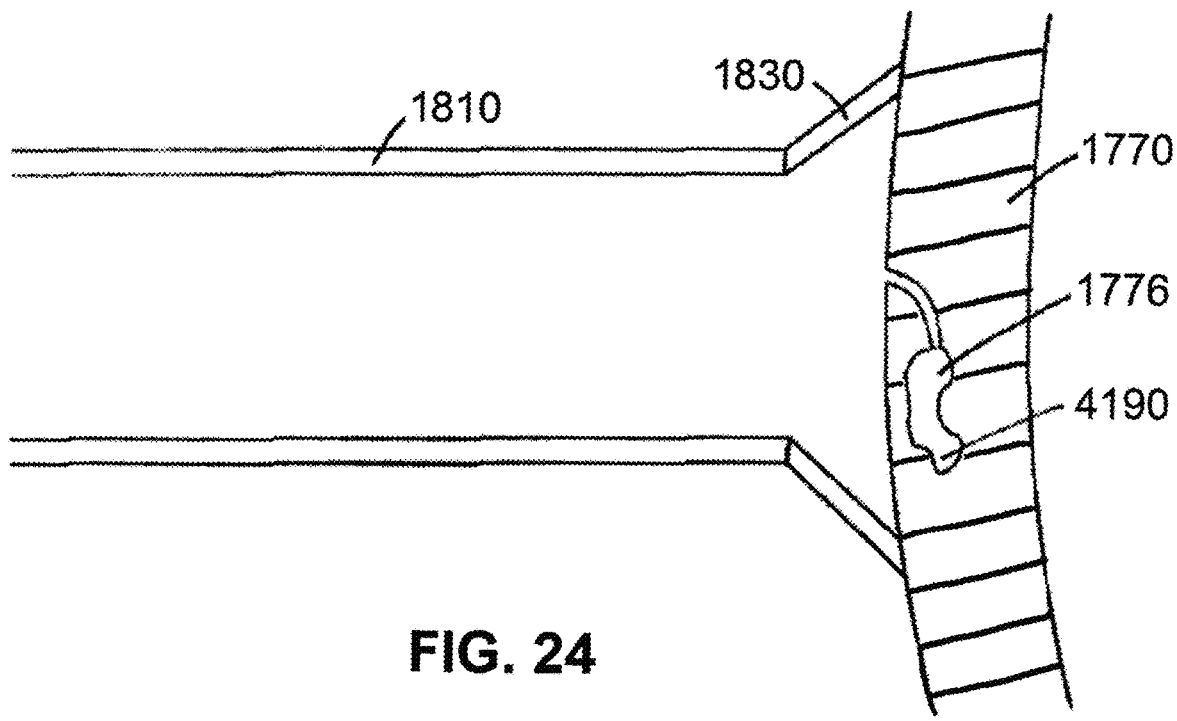
FIG. 24 shows a cut-away view of a distal portion of a system and no escaped substance, according to an exemplary embodiment of the present disclosure.

However, and even using a needle 1890 of the present disclosure to inject a bolus 4190 of substance 1776 into a tissue 1770, leakage of said substance 1776 may still occur, such as shown in FIG. 22, whereby escaped substance 4192 may have leaked out of tissue 1770 via puncture aperture 4195 upon or after withdrawal of needle 1890 from tissue 1770. However, and using an exemplary system 1805 of the present disclosure, suction through engagement catheter 1810 causes escaped substance 4192 to be withdrawn from the person through engagement catheter 1810, such as shown in FIG. 23, in the general direction of the arrow shown therein. Such a use of engagement catheter 1810 allows escaped substance 4192 to be safely withdrawn from the person versus potentially allowing said escaped substance 4192 to enter the bloodstream, for example, and potentially cause an embolus and/or generally cause escaped substance 4192 to enter an area of the body where escaped substance 4192 is not intended to be.

Suction can be applied as long as desired, such as for a duration whereby the user of system 1805 is comfortable that no additional substance 1776 will leak out of tissue 1770, such as whereby closure or relative closure of puncture aperture 4195 can occur, and/or whereby substance 1776 has an opportunity to congeal, coagulate, harden, etc. In such a situation, suction can cease, such as indicated within FIG. 24, whereby no escaped substance 4192 exists and bolus 4190 of substance 1776 remains within tissue 1770 as desired. Engagement catheter 1805 can then be safely withdrawn from the body, for example.

The present disclosure includes disclosure of a tension apparatus 2500, such as shown in FIGS. 25A, 25B, and 25C, which can be part of an exemplary system 1805 of the present disclosure, such as shown in FIG. 5, for example. An exemplary tension apparatus 2500 of the present disclosure is shown in FIG. 25A, whereby a distal portion 2502 of tension apparatus 2500 is shown extending out of a needle aperture 1920 of a needle 1890. Tension apparatus 2500 itself would comprise an elongated portion 2510 and a head portion 2512 at a distal end 2514 of elongated portion 2510. Head portion 2512 can comprise one or more arms 2520, such as shown in FIG. 25A, whereby a suction lumen 2530 extending along elongated portion 2510 and the one or more arms 2520 terminates at one or more suction openings 2532 at each of the one or more arms 2520. When suction/vacuum is applied through suction lumen 2530, and when the one or more arms 2520 contact a tissue 1770 (such as shown in FIG. 6, for example), the one or more arms 2520 can be suctionally attached to said tissue 1770.

Such an exemplary tension apparatus 2500 can be used to engage a tissue 1770 (or a wall 210 of a luminal organ 200), as referenced herein and as may be desired. Tension apparatus 2500 would be applied percutaneously, such as within needle 1890 or within other portions of an exemplary system 1805.

Exemplary tension apparatuses 2500 of the present disclosure, as referenced herein, are configured to fit within a lumen 4104 of a needle 1890. FIG. 25A shows portions of elongated portion 2510 of tension apparatus 2500 within lumen 4104 of needle 1890. FIG. 25B shows portions of tension apparatus 2500 within lumen 4104 of needle 1890, such as during delivery of the same (whereby arms 2520 of tension apparatus 2500 point in a direction proximal to a direction of delivery of needle 1890/tension apparatus 2500 and are generally next to (such as parallel to) a portion of elongated portion 2510 of tension apparatus 2500). FIG. 25C shows portions of tension apparatus 2500 being withdrawn back into lumen 4104 of needle 1890, such as after tension apparatus 2500 has been used to engage a tissue 1770, whereby arms 2520 of tension apparatus 2500 are generally distal to elongated portion 2510).

Should such a tension apparatus 2500 of the present disclosure be delivered within a lumen 4104 of a needle 1890, for example, said tension apparatus 2500 could be delivered such that the one or more arms 2520 are adjacent to an epicardial surface of the heart (an exemplary tissue 1770).

In an exemplary method of the present disclosure, a tension apparatus 2500 of the present disclosure can be delivered along with portions of an exemplary system 1805, such as a needle 1890 (and such as shown in FIG. 25B, for example), percutaneously to a desired location within the body. Pointed tip 4106 of needle 1890 could puncture a desired tissue 1770, and a distal portion 2502 of the tension apparatus 2500 could be extended from needle aperture 1920 of needle 1890 so that one or more arms 2520 of tension apparatus could extend outward (such as shown in FIG. 25A) and positioned adjacent to another tissue 1770, whereby suction through suction lumen 2530 could be used to suctionally affix the one or more arms 2520 of tension apparatus 2500 to said adjacent tissue 1770, as referenced in further detail herein. When the procedure is complete, suction through suction lumen 2530 could be stopped so that the one or more arms 2520 of tension apparatus 2500 are no longer suctionally affixed to the adjacent tissue 1770, and tension apparatus 2500 can be withdrawn, such as within lumen 4104 of needle 1890, as shown in FIG. 25C, for example.

Figure 25D:
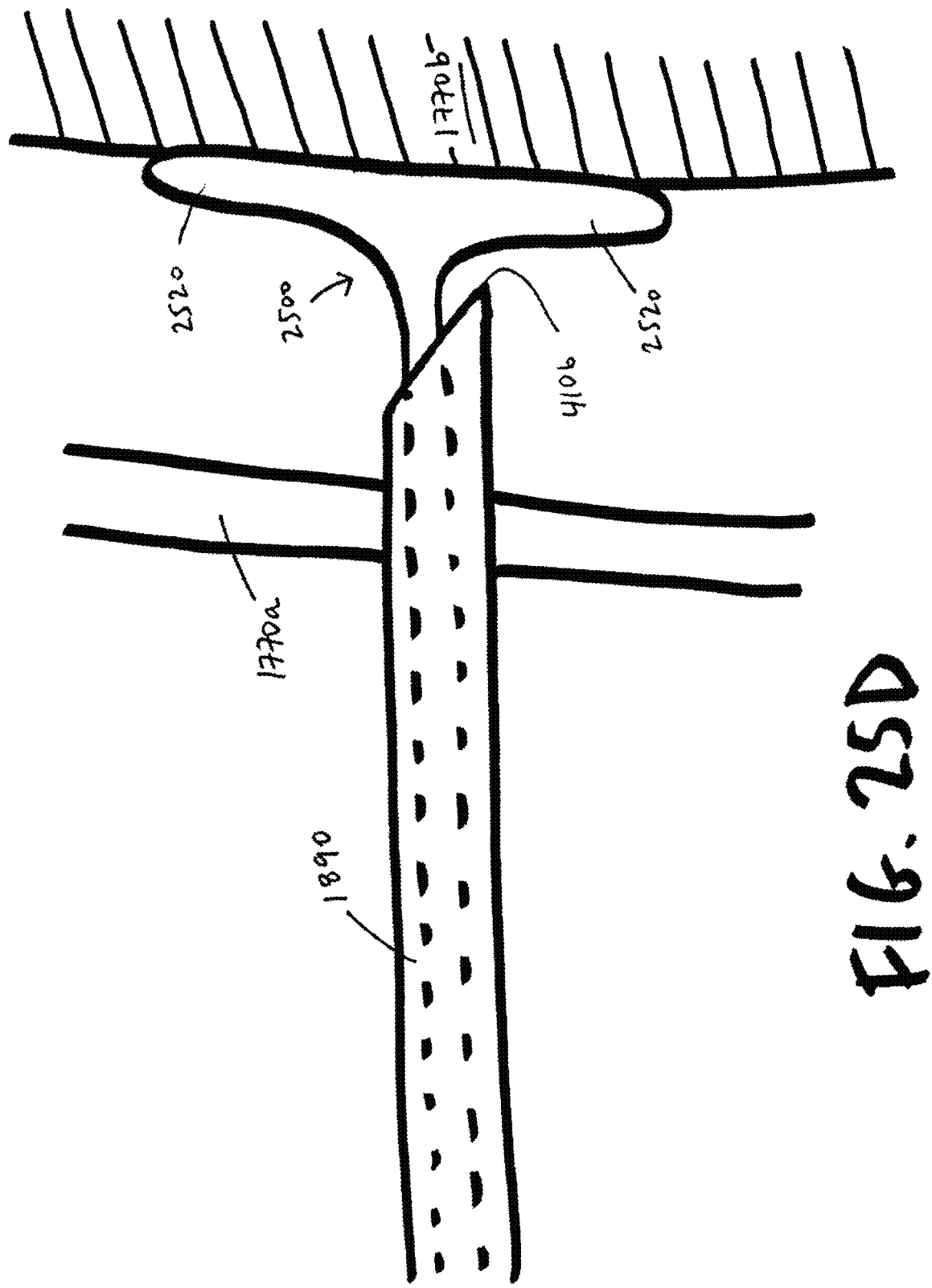
FIG. 25D shows a portion of a tension apparatus suctionally engaged to a tissue during use, according to an exemplary embodiment of the present disclosure.

In various embodiments, as referenced herein, a relatively larger needle 1890 could be used to deliver a tension apparatus 2500, and could be exchanged for a relatively smaller needle 1890, such as for use with intramural material 100 or substance 1776 delivery, as may be desired. Healthy myocardium, for example, is rather resilient regarding puncture wounds. Pacemaker leads, for example, readily perforate myocardium with a loss of pacing and sensing but not tamponade, but it is noted that in rare instances, for example, a pacemaker lead could accidentally perforate heart tissue (such as a right ventricle) causing hemorrhagic tamponade. In view of the same, a relatively larger needle 1890 could be used to deliver a tension apparatus through myocardium to an epicardial surface of the heart, as may be desired. FIG. 25D, for example, shows such a method, whereby a pointed tip 4106 of a needle 1890 is used to puncture and advance through myocardium (an exemplary tissue 1770a), and whereby tension apparatus 2500 is delivered out of needle aperture 1920 of needle 1890 so that arms 2520 of tension apparatus 2500 can suctionally engage an epicardial surface of the heart (an exemplary tissue 1770b).

The present disclosure also includes disclosure of ablation methods used in connection with various tissue engagement methods. It is noted that ablationists have a difficult challenge when attempting to create transmural lesions. If applied energy (during ablation) is too far reaching (too extensive), injury to surrounding tissue could occur, such as phrenic nerve palsy or esophageal-atrial fistula. Lower applied energy may be insufficient to create complete transmural lesions, leading to incomplete elimination of undesired wavefront propagation.

To address the same, the present disclosure includes disclosure of methods using both suction and ablation. In at least one embodiment, suction could be used to engage tissue with a device or system of the present disclosure, such as to pull ventricular or atrial tissue wall away from surrounding structures and to create a temporary shape to allow/permit ablation with a reduced risk of collateral damage, namely damage to surrounding tissues or structures. Such a temporary relocation of vascular tissue could be used with various types of ablation, such as cold ablation (cryoablation), hot ablation (such as using radiofrequency (RF) or laser ablation), and/or electrical ablation. Ablation could be surgical (e.g., excision), mechanical trauma (e.g. a small hammer or other device), electrical (heat or cold), or chemical (such as the use of alcohol in the interventricular septum for hypertrophic obstructive cardiomyopathy (HOCM)). Such a temporary relocation of vascular tissue could also be used with electroporation, namely the application of a field through a strong direct current (DC) gradient, which may make cell membranes more permeable to admitting a substance such as chemicals, pharmaceuticals, or DNA, for example. The energy required for electroporation is similar to, or may occur along with, electrical defibrillation, namely a brief, strong pulse of energy.

Figure 26A:
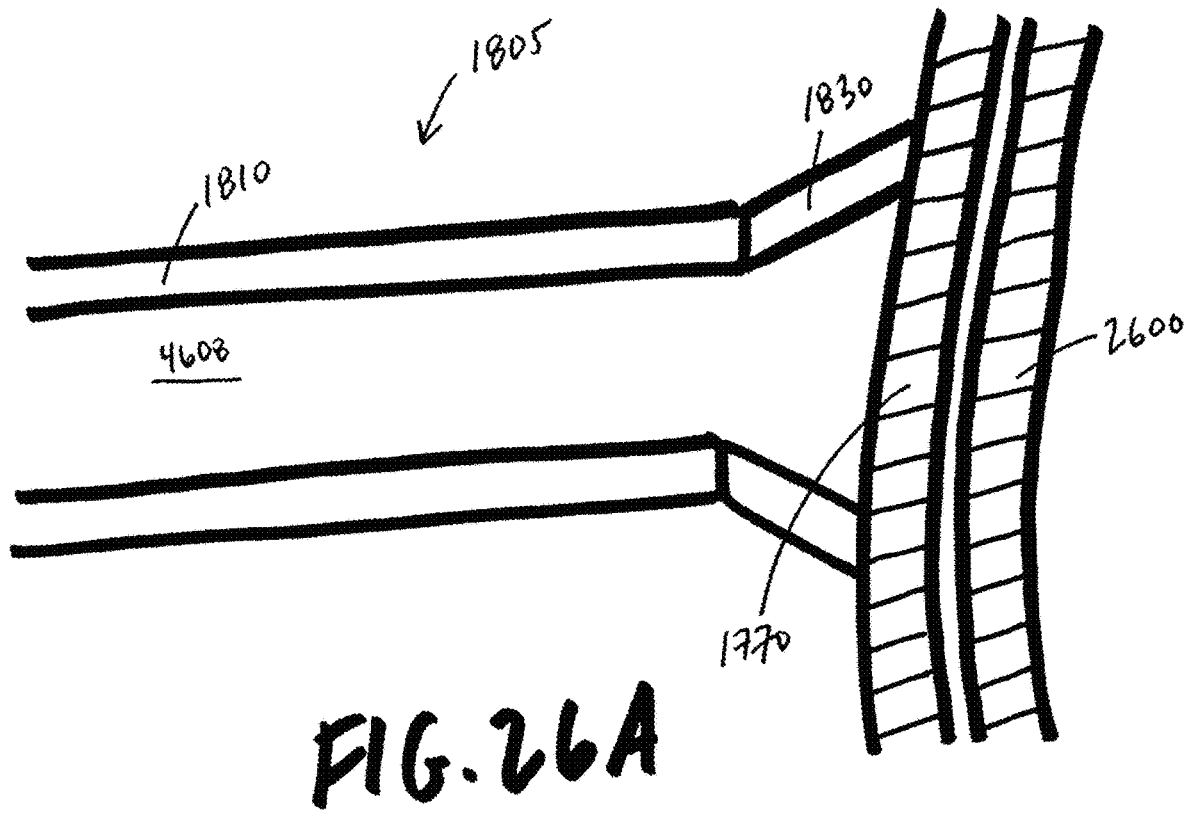
FIG. 26A shows a cutaway view of a distal portion of an engagement catheter suctionally engaged to a tissue, according to an exemplary embodiment of the present disclosure.
Figure 26B:
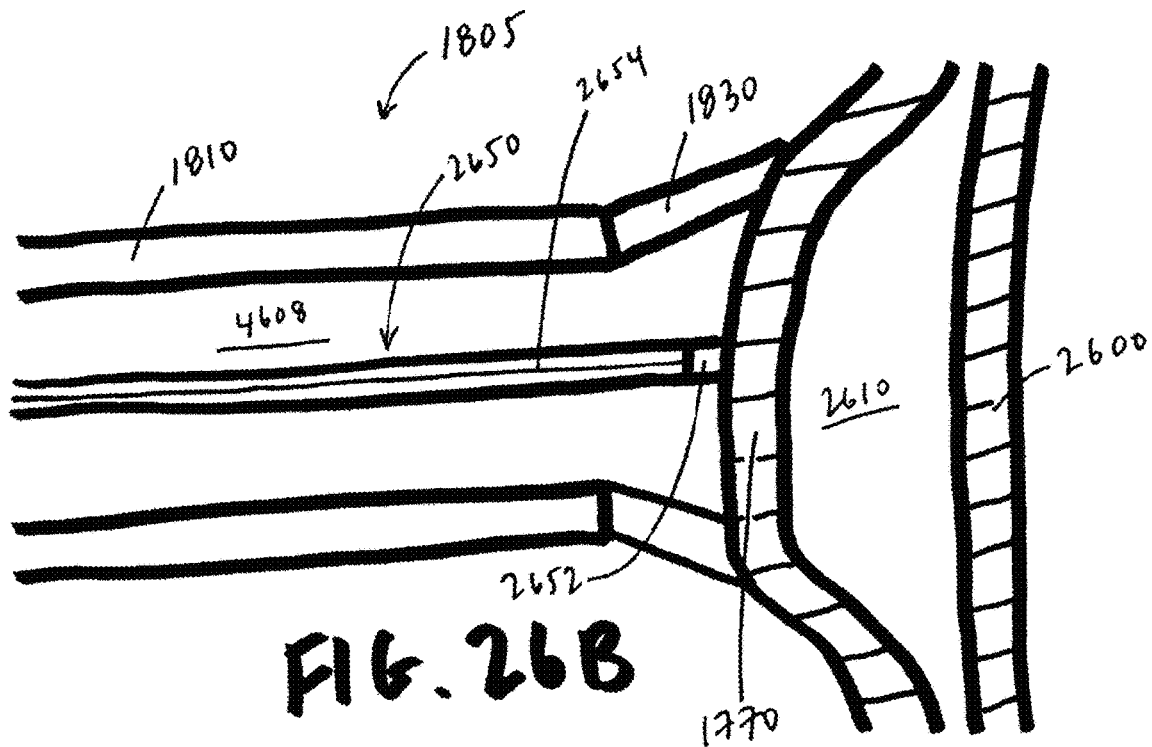
FIG. 26B shows a cutaway view of a distal portion of an engagement catheter suctionally engaged to a tissue with an ablation device within the engagement catheter, according to an exemplary embodiment of the present disclosure.

Such a method is demonstrated in FIGS. 26A and 26B. As shown therein, portions of an exemplary system 1805 are positioned within a mammalian body, such as within a blood vessel (an exemplary mammalian luminal organ 200), whereby a skirt or suction cup 1830 of an engagement catheter 1810 is positioned against a desired tissue 1770, whereby tissue 1770 is in front of a second tissue or organ 2600. Applying suction within a lumen 4608 of engagement catheter 1810 causes skirt or suction cup 1830 of engagement catheter 1810 to suctionally engage tissue 1770, such as shown in FIG. 26A. Retracting engagement catheter 1810, while under suction so that skirt or suction cup 1830 remains suctionally attached to tissue 1770, can cause portions of tissue 1770 to move away from second tissue or organ 2600, such as shown in FIG. 26B, creating a space 2610 between portions of tissue 1770 and portions of second tissue or organ 2600 or enlarging an smaller space 2610 between portions of tissue 1770 and portions of second tissue or organ 2600. An ablation device 2650, such as shown in FIG. 26B, can be advanced through lumen 4608 of engagement catheter 1810 so that an ablation element 2652 of ablation device 2650 contacts tissue 1770. Ablation element 2652, such as a cold ablation element 2652, a hot ablation element 2652, or an electrical ablation element 2652, can be operated to ablate portions of tissue 1770, whereby said ablation would either not affect second tissue or organ 2600, or would affect second tissue or organ 2600 at a lesser amount, by way of tissue 1770 being retracted away from second tissue or organ 2600 as shown in FIG. 26B. In at least one embodiment, ablation device 2650 comprises an electrical ablation device 2650, and ablation element 2652 comprises an electrical ablation element 2652, whereby power/energy can be delivered through, for example, an ablation wire 2654 extending along ablation device 2650 and coupled to ablation element 2652 so to power ablation element 2652 so that ablation element 2652 can ablate tissue 1770 as desired. Said ablation, for example, could be epicardial ablation (such as to treat recurrent ventricular tachycardia occurring after myocardial infarction), or another ablation procedure as desired, to treat a patient condition.

Delivery and positioning of portions of exemplary systems 1805 within the mammalian body are also important aspects of various medical procedures and methods using said systems 1805. For example, knowing the location of portions of exemplary systems 1805 within the body, such as knowing when portions of said systems 1805 are located within a wall 210 of a luminal organ 200. As referenced herein, various indicators can be used, such as to determine or measure suction flow and/or pressure, temperature, impedance, etc., within portions of said systems 1805.

FIG. 27 shows a distal portion of an engagement catheter 1810, which can be part of an exemplary system 1805 of the present disclosure. As shown therein, engagement catheter 1810 can comprise one or more internal sensors 2700 positioned within lumen 4608 of engagement catheter 1810 and/or positioned within lumen 2750 of skirt or suction cup 1830, whereby lumen 2750 is defined as the area within skirt or suction cup 1830 and whereby lumens 2750 and 4608 are contiguous lumens. One or more sensor wires 2702 coupled to the one or more internal sensors 2700 and to a console 3250 (referenced in further detail herein) can extend along portions of engagement catheter 1810, such as shown in FIG. 27, so to provide power/energy to operate internal sensors 2700. Internal sensors 2700 may be, for example, pressure sensors, temperature sensors, and/or impedance sensors, used to obtain pressure, temperature, and/or impedance data. For example, a pressure sensor (exemplary internal sensor 2700) could obtain pressure data indicating pressure changes due to fluid removal or introduction from within engagement catheter 1810 and/or skirt or suction cup 1830. Said pressure data could, for example, be atrial pressure data, whereby changes in atrial pressure can indicate whether or not the internal sensor 2700 is located within an atrial cavity of within atrial tissue. A temperature sensor (exemplary internal sensor 2700) could obtain temperature data indicating changes in temperature due to fluid removal or introduction from within engagement catheter 1810 and/or skirt or suction cup 1830. Impedance sensors (exemplary internal sensors 2700) could obtain impedance data indicating changes in impedance due to fluid removal or introduction, or whether an electrode (an exemplary internal sensor 2700) is located within a fluid or within a tissue, or fluid mixing (such as blood and saline), and the like, from within engagement catheter 1810 and/or skirt or suction cup 1830. For example, saline (or another fluid having a different conductance and/or temperature than that of native fluid (such as blood) within the body and within portions of engagement catheter 1810) could be introduced from within needle 1890 and out of needle aperture 1920 and detected using one or more internal sensors 2700. Ultrasound, or another mechanism to detect the presence of a bolus of saline within the body, could be used such as while needle 1890 is being advanced along with engagement catheter 1810 (or other portions of systems 1085), and, for example, one or more boluses of saline injected out of needle aperture 1920 during advancement could be detected using ultrasound so to determine location of pointed tip 4106 and other portions of system 1805 positioned relative to said needle 1890. Seeing a small bolus of saline that is stationary and moving in concert with a vessel wall, for example, could be used to confirm intramural needle 1890 location and suitability for potential therapeutic injection of a drug, for example, through needle 1890.

The present disclosure also includes disclosure of devices, systems, and methods useful to control the extent of needle 1890 puncture. For example, and as shown in FIG. 1, a needle 250 (or 1890) is shown puncturing a wall 210 of a luminal organ 200, whereby a material 100 can be injected through needle 250 and out of needle aperture 290 (or 1920) into said wall 210, such as to reinforce said wall 210, such as shown in FIG. 2. As referenced herein, the ability to control the extent of needle 250, 1890 puncture is also important in certain instances.

Figure 28:
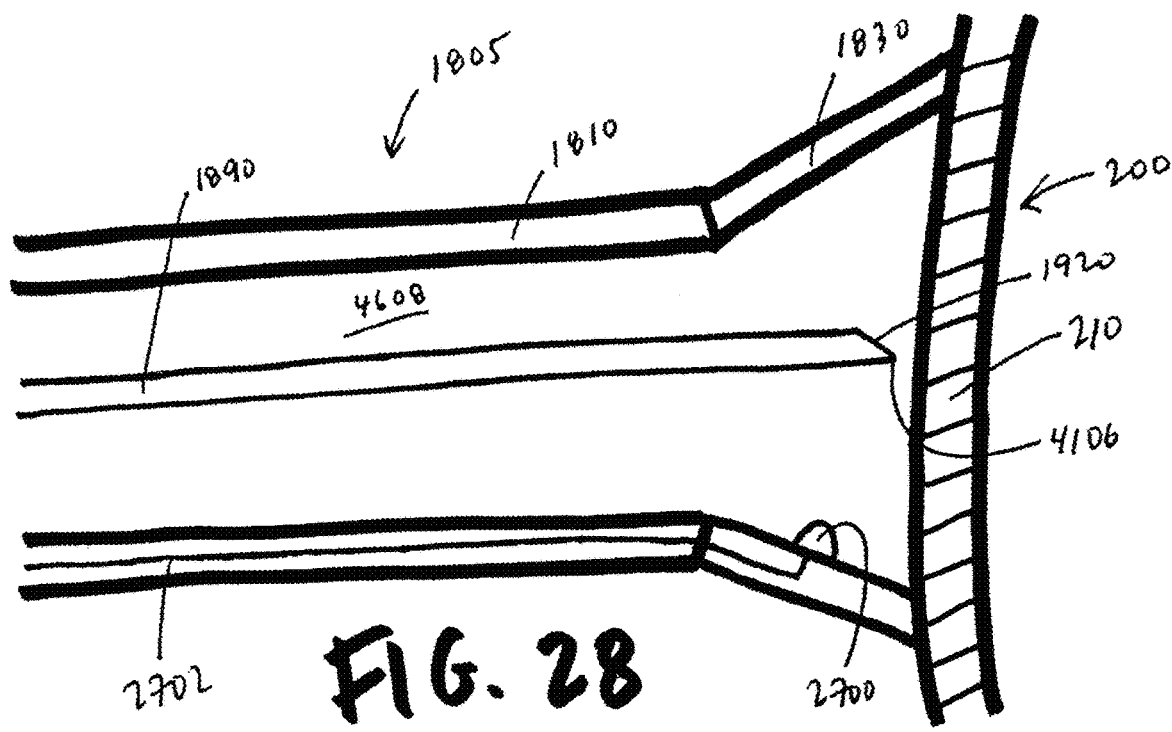

FIG. 28 shows portions of an exemplary system 1805 positioned adjacent to a wall 210 of a vessel 200 (or adjacent to a tissue 1770, such as shown in FIG. 6. A needle 1890 is shown within engagement catheter 1810, whereby pointed tip 4106 of needle 1890 does not contact or puncture wall 210 of luminal organ 200. Portions of engagement catheter 1810 and needle 1890, for example, could be retained so that portions thereof move consistent with one another (such as distal portions of engagement catheter 1810 and needle 1890 moving at the same rate within the body). An initial application of suction (vacuum) through lumen 4608 of engagement catheter 1810 can cause skirt or suction cup 1830 to suctionally attach to wall 210 of luminal organ 210 (or to tissue 1770, as referenced herein), such as shown in FIG. 28. Application of stronger and/or longer (prolonged) suction through lumen 4608 can then cause pointed tip 4106 of needle 1890 to puncture wall 210 of luminal organ 200. An extent of said puncture and subsequent advancement of pointed tip 4106 of needle 1890 can therefore be controlled and/or determined by way of the extent of suction through lumen 4608 of engagement catheter 1810, as, for example, skirt or suction cup 1830 would collapse due to increased suction, and if portions of needle 1890 and engagement catheter 1810 are retained relative to one another, collapsing of skirt or suction cup 1830, and therefore movement of a distal portion of engagement catheter 1810 toward wall 210 of luminal organ 200, would also cause pointed tip 4106 of needle 1890 to move toward said wall 210 of luminal organ 200, puncturing the same. Pressure changes due to suction within lumen 4608 of engagement catheter could also be determined using an internal sensor 2700 configured as a pressure sensor 2700, for example, such that very precise changes in suction/vacuum can be determined to precisely control needle 1890 puncture and advancement, so to deliver a material 100 or substance 1776 within wall 210 or tissue 1770 as desired.

Skirts or suction cups 1830 can be considered as flanges, and may be constructed or positioned upon various portions of systems 1805 of the present disclosure, such as engagement catheters 1810, sheaths 1800, needles 1890, and the like. Skirts or suction cups 1830 of said devices can be positioned against walls 210 of luminal organs 200 as referenced herein, such as percutaneously or intravascularly, as generally referenced herein, and or surgically, as described in further detail herein.

Figure 29:
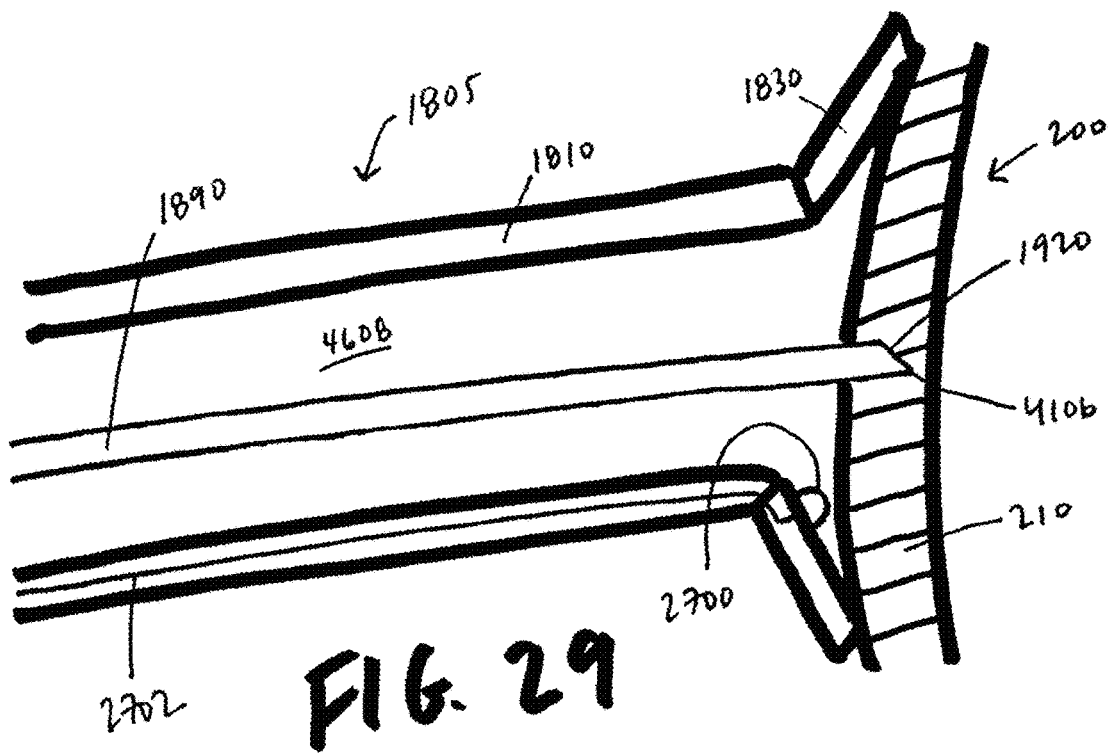
FIG. 29 shows a cutaway view of a distal portion of an engagement catheter suctionally engaged to a tissue with a needle therein perforating said tissue, according to an exemplary embodiment of the present disclosure.
Figure 30:
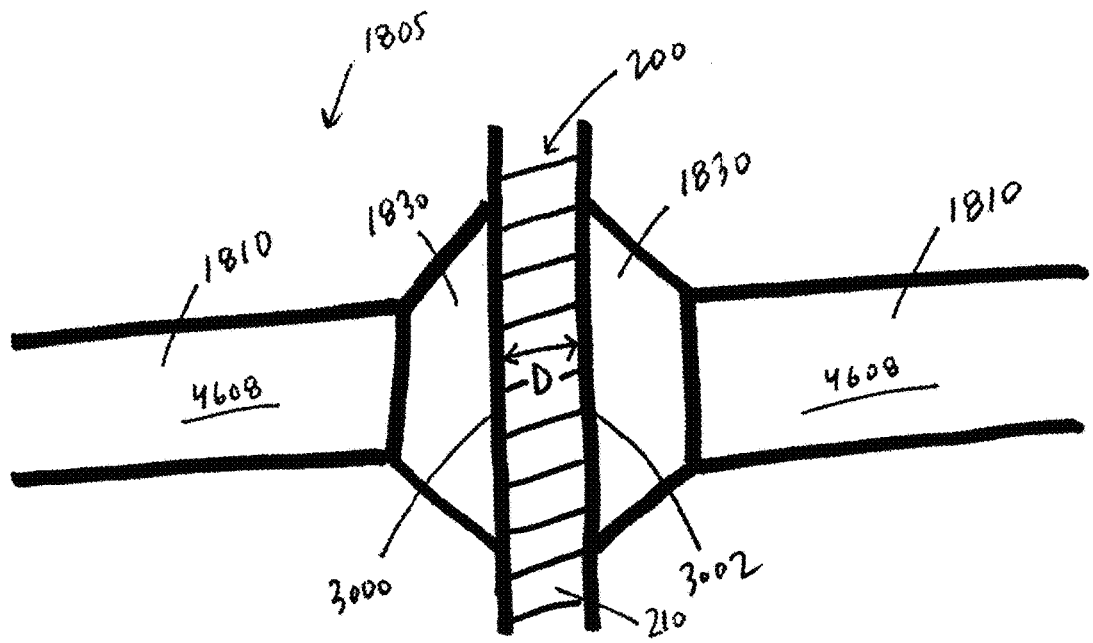
FIG. 30 shows two engagement catheters suctionally engaged to opposing sides of a tissue, according to an exemplary embodiment of the present disclosure.
Figure 31:
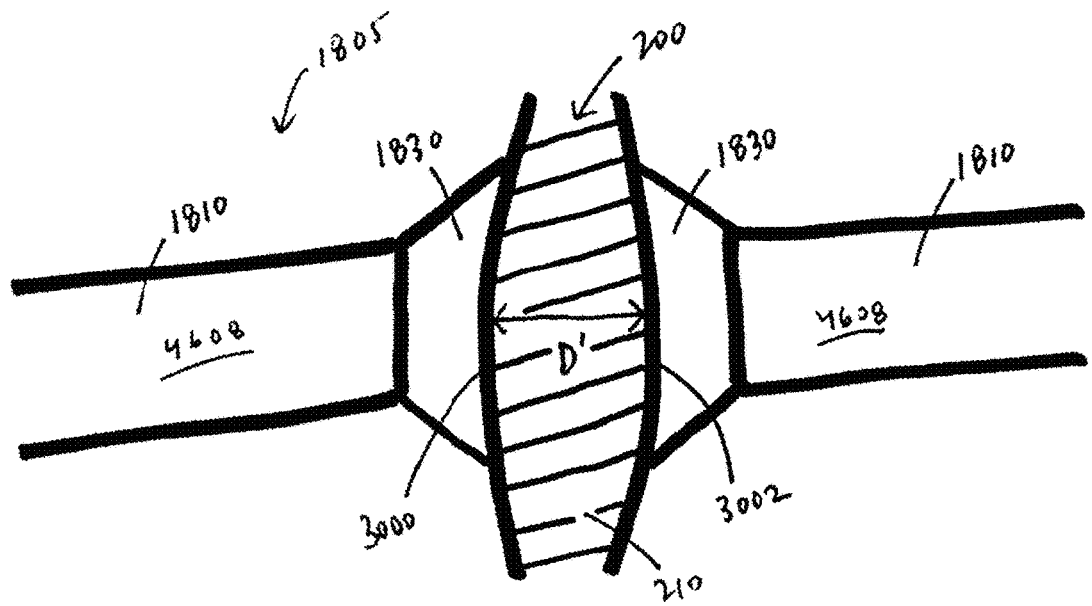
FIG. 31 shows two engagement catheters suctionally engaged to opposing sides of a tissue and pulled in opposite directions to stretch said tissue, according to an exemplary embodiment of the present disclosure.

FIG. 30 shows a wall 210 of a luminal organ 200 having an inner surface 3000 and an opposing outer surface 3002, whereby a native distance D is shown as being the thickness of wall 210 at a particular location, whereby the thickness is the distance D between surfaces 3000, 3002. An exemplary system 1805 of the present disclosure can comprise two devices having flanges, such as two engagement catheters 1810, two sheaths 1800, etc., each having a skirt or suction cup 1830 (an exemplary flange), whereby, for example, a first engagement catheter 1810 having a first skirt or suction cup 1830 can be delivered percutaneously and/or intravascularly so that skirt or suction cup 1830 can contact inner surface 3000 of wall 210, and whereby a second engagement catheter 1810 having a second skirt or suction cup 1830 can be positioned surgically, for example (or also delivered percutaneously and/or intravascularly, as the case may be), to the opposing outer surface 3002, as shown in FIG. 30, so to create a sandwich effect about luminal organ 200. Application of suction (vacuum) within lumens 4608 of engagement catheters 1810 can initially cause skirts or suction cups 1830 to suctionally engage surfaces 3000, 3002, and further application of suction (vacuum), coupled with gentle or mild retraction of engagement catheters 1810 away from said surfaces 3000, 3002, can cause a slight local stretching or expansion of wall 210 of luminal organ 200, such as shown in FIG. 31, whereby a distance D' between surfaces 3000, 3002 is larger than the original native distance D as shown in FIG. 30. Said stretching or expansion of tissue could temporarily relive wall 210 stress, such as from the contractile nature of said tissue, and also be coupled with delivery of a material 100 or substance 1776 using a needle 250, 1890, as referenced herein. The larger distance D' also allows for relatively easier positioning of pointed tip 4106 within wall 210 of tissue 200, such as shown in FIG. 29, as wall 210 is effectively thicker due to said stretching.

Figure 32:
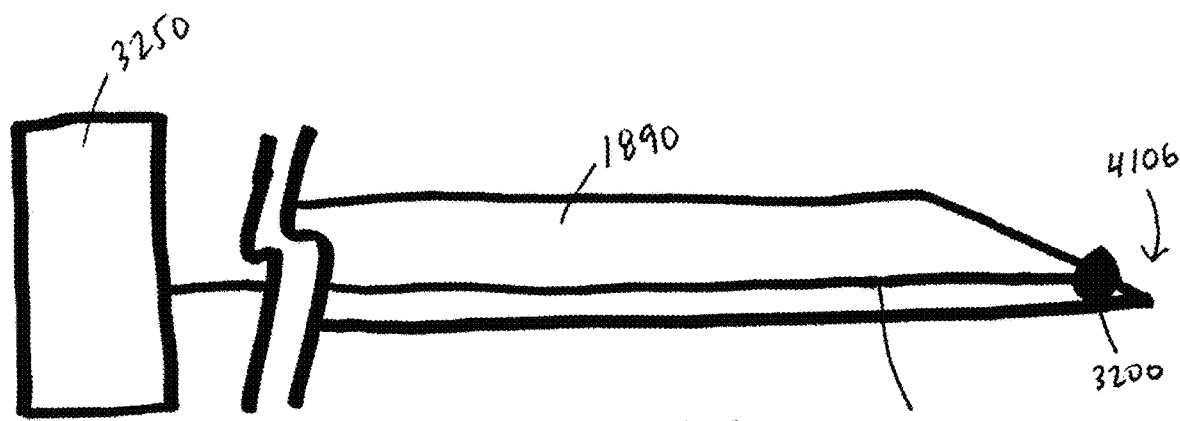
FIG. 32 shows a distal portion of a needle having an electrode coupled thereto, according to an exemplary embodiment of the present disclosure.

The present disclosure also includes disclosure of needles 250, 1890, whereby said needles comprise one or more electrodes configured to obtain electrocardiogram (ECG) data within the body. Electrocardiogram refers to a proscribed set of electrodes and method of signal extraction from a body surface, such as a human body surface. Electrophysiologists use electrograms, signals recorded from electrodes within the body. For example, and as shown in FIG. 32, an exemplary needle 1890 (or 250) comprises at least one electrode 3200 at or near pointed tip 4106, wherein said electrode 3200 is configured to obtain ECG data. An electrode wire 3202 coupled to electrode 3200 could extend along at least a portion of needle 250, 1890 and provide power/energy to electrode 3200 and/or transmit ECG data from electrode 3200 to, for example, a console 3250 (such as a hospital computer/console or other electronic equipment known or used in the art that is configured to connect to other medical devices, such as a catheters, wires, leads, and the like). A console 3250 can connect to various devices of the present disclosure, and can form part of an exemplary system 1805. An exemplary electrode 3200 of the present disclosure could also be an exemplary sensor 2700 of the present disclosure, as referenced herein, such as, for example, a pressure sensor, a temperature sensor, and/or an impedance sensor, used to obtain pressure, temperature, and/or impedance data.

Such a needle 1890 (or 250), such as shown in FIG. 32, can be used consistent with the present disclosure, and can also be used to determine, for example, whether or not pointed tip 4106 of needle 1890, 250 is positioned within tissue 1770 (or a wall 210 of a luminal organ 200) or not, such as being positioned within the bloodstream not in a tissue 1770 or a wall 210 of a luminal organ 200. Such a needle 1890 (or 250) could also be used, for example, to differentiate whether or not pointed tip 4106 of needle 1890, 250 is positioned within myocardial scar tissue or myocardial tissue that is not scarred, as, for example, a relatively lower electrogram amplitude can indicate a myocardial scar, or a border zone of a scar, an area of heterogeneous conduction properties that may predispose a patient to cardiac arrhythmia, or other insult as compared to healthy or unscarred myocardial tissue. Furthermore, delayed depolarization timing relative to electrograms measured and recorded from nearby parts of the heart can indicate a blockage or other scar. As such, electrophysiological indicia could be an additional source to identify areas to apply/administer or avoid delivering a therapeutic regimen (material 100 or substance 1776, for example). Electrogram data obtained by electrode 3200 could therefore also provide another indication of tissue 1770 engagement.

Figure 33:
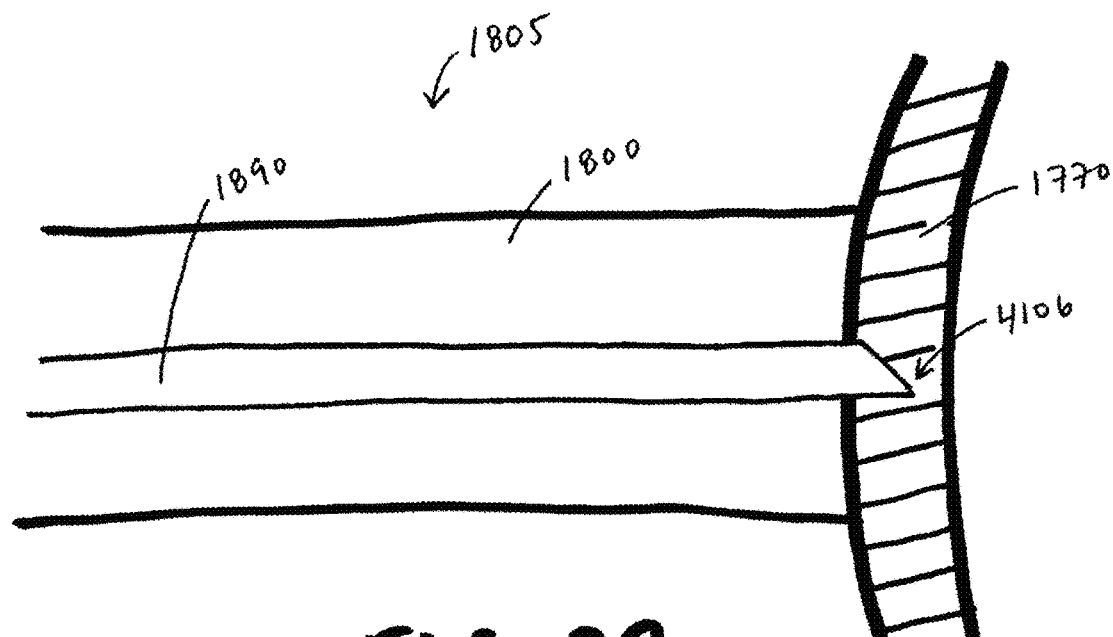
FIG. 33 shows a distal portion of a sheath having a needle therein whereby said needle is piercing a tissue, according to an exemplary embodiment of the present disclosure.

FIG. 33 shows, for example, use of portions of an exemplary system 1805 of the present disclosure, whereby sheath 1800 (or an engagement catheter 1810, not shown in FIG. 33) can be stiff or relatively stiff, and able to exert a force against a tissue 1770 (or a wall 210 of a luminal organ 200). Instead of suction through engagement catheter 1810 (as shown in FIG. 29 and referenced herein) or through sheath 1800, or along with said suction, sheath 1800 (or engagement catheter 1810) could exert a force against the myocardium (an exemplary tissue 1770, for example), and ventricular contraction could cause pointed tip 4106 of needle 1890 to penetrate said myocardium when sheath 1800 (or engagement catheter 1810) is held relative to needle 1890, 250. Such perforation would occur, for example, due to ventricular contraction moving tissue 1770 at the location of sheath 1800 (or engagement catheter 1810) relative to said sheath 1800 or engagement catheter 1810 when sheath 1800 or engagement catheter 1810 is positioned against tissue 1770. This is yet another method to control perforation of tissue 1770 using a needle 1890, 250 of the present disclosure.

The various systems 1805 of the present disclosure and portions thereof can be used to facilitate material 100 or substance 1776 delivery to septal tissue (an exemplary tissue 1770), such as to the ventricular septum or the atrial septum, also known as the interventricular and interatrial septa. Suction engagement, such as through a lumen 4608 of an engagement catheter 1810, in connection with material 100 or substance 1776 delivery, for example, can be used to close a patent foramen ovale (PFO) or treat an atrial septal defect (ASD), for example.

The present disclosure also includes disclosure of an engagement catheter 1810 such as configured in FIG. 34. As shown in FIG. 34, engagement catheter 1810 has a lumen 4106 defined therethrough, whereby lumen 4608 is referred to as a delivery lumen 4608. A plurality of peripheral lumens 3400, in such an embodiment, are also defined within engagement catheter 1810, whereby at least one peripheral lumen 3400 is used for suction/vacuum (so to facilitate tissue engagement of engagement catheter 1810 using suction, as referenced herein), and whereby at least one peripheral lumen 3400 contains a conductive cable or wire 3410 therein, whereby conductive cable or wire 3410 directly, or indirectly by way of an electrode 3200 coupled thereto at the end of conductive cable or wire 3410, can be used to stimulate cardiac tissue, record or detect electrical activity (such as ECG data, referenced herein), and/or used for electroporation to introduce genetic material into beating heart tissue, for example.

Suction engagement could be, for example, suction engagement to an endocardium of a heart (an exemplary tissue 1770). While under suction, conductive cable or wire 3410, or an electrode 3200 coupled thereto, could contact tissue 1770 and be used as referenced herein. Delivery lumen 4106 could be used to introduce a material 100 or substance 1776 into said tissue 1770, either alone, using a needle 1890, 250, or a delivery catheter 1840, for example.

In at least one embodiment of the present disclosure, two or more peripheral lumens 3400 each contain a conductive cable or wire 3410, whereby said conductive cable or wire 3410 or an electrode 3200 coupled thereto, can be used as referenced herein, and can also be used to obtain ECG data indicating direction of an activation wavefront in cardiac tissue, for example. Timing and amplitude of unipolar ECG recordings are markers of an advancing wavefront providing information regarding direction of the wavefront relative to the orientation of said engagement catheter 1810.

The present disclosure includes disclosure of a tension apparatus 2500, such as shown in FIGS. 35E, 35F, and 35G, which can be part of an exemplary system 1805 of the present disclosure, such as shown in FIG. 5, for example. Other portions of an exemplary system 1805 of the present disclosure, such as an engagement catheter 1810, can also be used as referenced herein and/or as provided in further detail below.

Figure 35C:
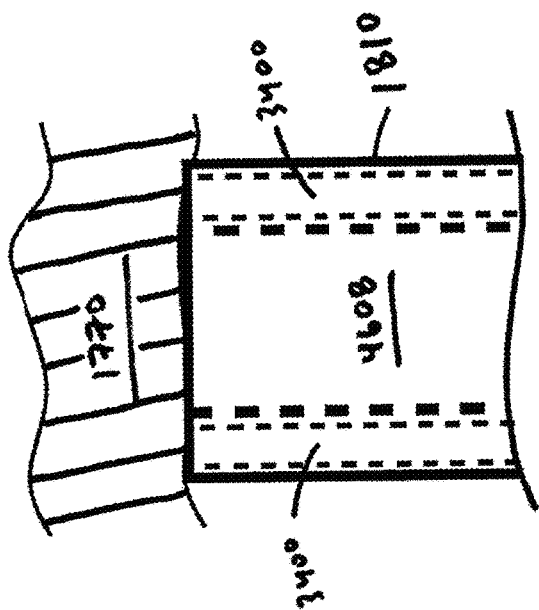
FIG. 35C shows a distal portion of an engagement catheter suctionally engaged to a tissue, according to an exemplary embodiment of the present disclosure.
Figure 35B:
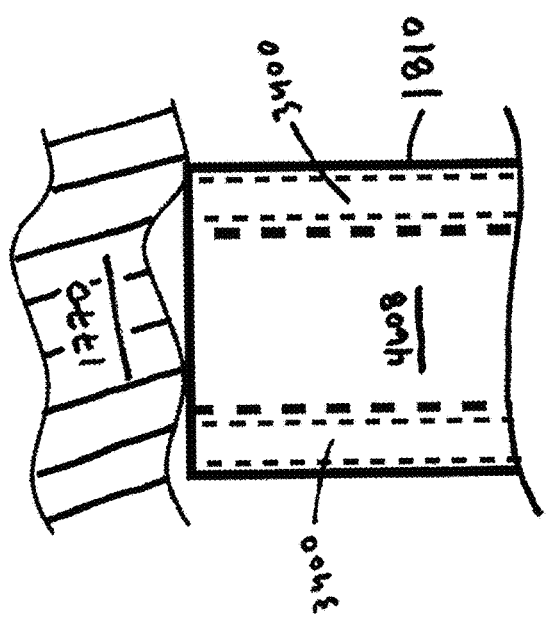
FIG. 35B shows a distal portion of an engagement catheter contacting a tissue, according to an exemplary embodiment of the present disclosure.
Figure 35A:
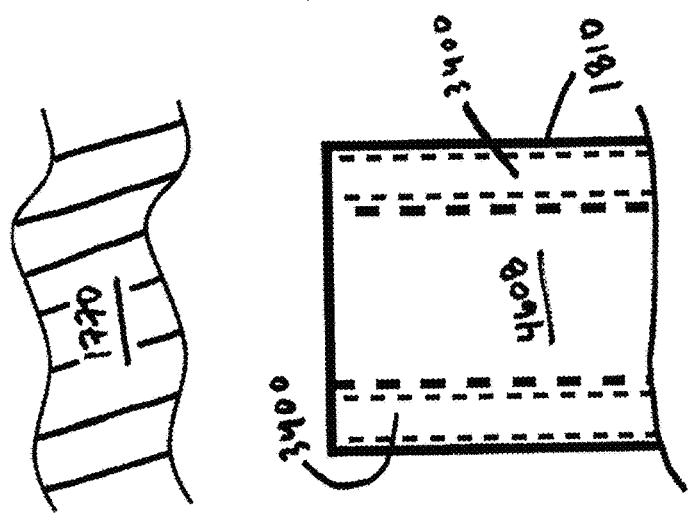
FIG. 35A shows a distal portion of an engagement catheter approaching a tissue, according to an exemplary embodiment of the present disclosure.

FIG. 35A shows a tissue 1770 (or a wall 210 of a luminal organ 200) having an irregular surface, with a distal portion of an engagement catheter 1810 approaching said tissue 1770. Engagement catheter, as referenced herein, can have a lumen 4608, also referred to as a central lumen or a delivery lumen in this embodiment, defined therethrough, and can have at least one peripheral lumen 3200 defined therethrough, such as shown in FIG. 34. FIG. 35B shows the distal end of engagement catheter 1810 positioned adjacent an interior surface of tissue 1770 (or wall 210 of luminal organ 200). If luminal organ 200 were a heart, for example, the adjacent interior surface would be an endocardium or endocardial surface. FIG. 35C shows engagement catheter 1810 being suctionally attached to tissue 1770, whereby suction/vacuum is applied within the one or more peripheral lumens 3400, such as via two peripheral lumens 3400 in the engagement catheter 1810 embodiment shown in the figure. Said suction/vacuum provides attachment between engagement catheter 1810 and the interior surface of tissue 1770.

In FIG. 35D, a needle 1890 is shown as being is extended through the central lumen (lumen 4608) of engagement catheter 1810. Needle can be used to puncture the luminal organ (tissue 1770) interior surface, penetrate the wall of the luminal organ (tissue 1770), and reach a space outside the luminal organ 1770 wall.

An exemplary tension apparatus 2500 of the present disclosure as shown in FIG. 35E can then be used, whereby a distal portion 2502 of tension apparatus 2500 (as shown in FIG. 35F) is shown extending out of a needle aperture 1920 of a needle 1890. Tension apparatus 2500 can be as described herein. Head portion 2512 (as shown in FIG. 35G) of tension apparatus 2500 can comprise one or more arms 2520, such as shown and identified in FIG. 35G, whereby a suction lumen 2530 (as shown and identified in FIG. 35E) extending along elongated portion 2510 and the one or more arms 2520 terminates at one or more suction openings 2532 (as shown and identified in FIG. 35E) at each of the one or more arms 2520. Suction openings 2532 can be located along the one or more arms 2520 (as shown in FIG. 35G) on a relative proximal side of said one or more arms 2520 so to allow potential suctional engagement of an opposite side of tissue 1770 that is being suctionally engaged using engagement catheter 1810, such as shown in FIGS. 35F and 35G. When suction/vacuum is applied through suction lumen 2530, and when the one or more arms 2520 contact a tissue 1770 (such as shown in FIGS. 35F and 35G, for example), the one or more arms 2520 can be suctionally attached to said tissue 1770.

Tension apparatus 2500, as shown in FIG. 35E, has arms 2520 deployed (such as in a perpendicular or relatively perpendicular configuration to elongated portion 2510) out of needle aperture 1920 of needle 1890. Needle 1890 can then be withdrawn into engagement catheter 1810, so to allow arms 2520 of tension apparatus 2500 to contact tissue 1770 when tension apparatus 2500 is retracted toward tissue 1770, such as shown in FIG. 35F. Should tissue 1770 be heart tissue, for example, arms 2520 could contact the epicardial surface of the heart. Application of suction through suction lumen 2530 allows arms 2520 to become suctionally engaged to tissue 1770.

When suction is applied through peripheral lumens 3400 of engagement catheter 1810, so to be suctionally engaged to a proximal side of tissue 1770, and when suction is also applied through suction lumen 2530 of tension apparatus 2500 when arms 2520 contact a distal side of tissue 1770, relative movement of arms 2520 of tension apparatus in a direction opposite a distal end of engagement catheter 1810 can cause a distance between arms 2520 and engagement catheter 1810 to increase. This can be accomplished by applying a gentle force to extend tension apparatus 2500 outward relative to engagement catheter 1810. The increased distance stretches tissue 1770 captured between the engagement catheter 1810 and portions of tension apparatus 2500, such as shown in FIG. 35G. Since both the tension apparatus 2500 and engagement catheter 1770 are engaged to their respective luminal organ walls (walls of tissue 1770, for example), as the distance between the tension apparatus 2500 and engagement catheter 1770 increases, the interior and exterior walls of tissue 1770 are drawn apart.

One or more sensors 2700 and/or electrodes 3200, as referenced herein, could be coupled to engagement catheter 1810 (such as shown in FIGS. 27, 28, and 29), needle 1890 (such as shown in FIG. 32), sheath 1800, tension apparatus 2500, or other portions of systems 1805, as may be desired, such as to obtain electrogram data, for example. A comparison of electrograms collected from electrodes 3200 and/or sensors 2700 located on the interior and exterior surfaces of the luminal organ (tissue 1770 or wall 210 of luminal organ 200) provide information relative to transmural conduction properties that may aid in recognition and identification of damaged or diseased tissue 1770, for example.

Once the needle 1890 has been retracted, a material 100 or substance 1776 may be delivered to the luminal organ wall (tissue 1770) via lumen 4608 of engagement catheter 1810 through a puncture wound (opening) resulting from delivery into and retraction of needle 1890 from tissue 1770. Maintaining separation between arms 2520 of tension apparatus 2500 and engagement catheter 1810 affords a stabilized and stretched luminal organ (tissue 1770) wall to facilitate delivery of a material 100 or substance 1776. Electroporation may be used to facilitate delivery of a material 100 or substance 1776, for example. A requisite electric field for electroporation may be delivered between electrodes 3200 or sensors 2700 on the engagement catheter 1810, needle 1890, sheath 1800, tension apparatus 2500, or other portions of systems 1805, as may be desired, or indifferent electrode(s) 3200 or sensors 2700 placed directly upon the patient. Such an indifferent electrode 3200 or sensor 2700 may be a large plate electrode placed on the patient body surface or within the patient. The indifferent electrode (electrode 3200 or sensor 2700) can have a large surface area, such as compared to a surface area of an electrode 3200 or sensor 2700 on the engagement catheter 1810, needle 1890, sheath 1800, tension apparatus 2500, etc.

Exemplary sheaths 1800, engagement catheters 1810, needles 1890, and/or tension apparatus 2500 may be further enhanced with electrodes 3200 or sensors 2700 to facilitate navigation and location within the body of a patient. Such electrodes 3200 or sensors 2700 may be configured as electrodes, coils, magnets, metal, or other materials with a specific imaging opacity, as may be desired.

After the desired procedure has been completed, tension apparatus 2500 can be withdrawn from the body through the engagement catheter 1810. As shown in FIG. 35H, for example, suction through suction lumen 2530 of tension apparatus 2500 can be stopped, releasing arms 2520 from tissue 1770. Withdrawal of tension apparatus 2500 can be performed, and arms 2520 can fold toward one another, as shown in FIG. 35H, to facilitate removal of tension apparatus 2500 through engagement catheter 1810.

Systems 1805, such as referenced herein, can provide a user of said system(s) 1805 with the certainty that the substance 1776 delivered to the tissue 1770 of interest, such as, for example, to ensure that stem cells (an exemplary substance 1776) is delivered to a myocardium (an exemplary tissue 1770), so that substance 1776 can treat the patient as desired.

Other uses of exemplary delivery mechanisms 300 and/or systems 1805 are also contemplated herein and within the present disclosure, such as during known or developed medical procedures whereby suction engagement of a catheter to a tissue or organ 5600 is part of the procedure.

While various materials and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A tension apparatus for suctionally engaging and stabilizing tissue, comprising:
    an elongated portion; and
    a head portion at a distal end of the elongated portion, the head portion comprising two or more arms deployed perpendicular to the elongated portion, wherein the two or more arms are configured to bend so that during delivery of the tension apparatus within a needle, the two or more arms are next to a portion of the elongated portion;
    wherein the elongated portion and the head portion comprising two or more arms, of the tension apparatus, are all configured to extend out of a single needle aperture of a needle; and
    whereby a suction lumen extending along the elongated portion and extending through the two or more arms terminates at one suction opening on each of the two or more arms; the tension apparatus configured such that when vacuum is applied through the suction lumen, the suction opening on each of the two or more arms suctionally engages and stabilizes the tissue.

2. The tension apparatus of claim 1, wherein the tension apparatus is further configured to fit at least partially within the needle.

3. The tension apparatus of claim 1, wherein the two or more arms are configured to bend so that during retraction of the tension apparatus within the needle, the two or more arms are distal to the elongated portion.

4. The tension apparatus of claim 1, wherein the tension apparatus is further configured so that when positioned at least partially within the needle that punctures a first tissue, the two or more arms can extend out of the single needle aperture of the needle distal to the first tissue and suctionally attach to a second tissue distal to the first tissue under vacuum.

5. The tension apparatus of claim 1, wherein the suction opening on each of the two or more arms are distally located along the two or more arms so that the suction opening can contact a tissue located distal to the two or more arms.

6. The tension apparatus of claim 1, wherein the suction opening is proximally located along the two or more arms so that the suction opening can contact a tissue located proximal to the two or more arms.

7. The tension apparatus claim 1, comprising part of a system for suctionally engaging and stabilizing tissue, the system further comprising:
    the needle configured to at least partially enclose the tension apparatus.

8. The tension apparatus of claim 7, comprising part of the system for suctionally engaging and stabilizing tissue, the system further comprising:
    an engagement catheter configured to at least partially enclose the needle.

9. A method, comprising:
    introducing a needle into a mammalian body, the needle having at least a portion of a tension apparatus therein, the tension apparatus comprising:
        an elongated portion, and
        a head portion at a distal end of the elongated portion, the head portion comprising two or more arms, wherein the two or more arms are configured to bend so that during delivery of the tension apparatus within a needle, the two or more arms are next to a portion of the elongated portion,
        whereby a suction lumen extending along the elongated portion and extending through the two or more arms terminates at a suction opening on each of the two or more arms;
    advancing the tension apparatus within the needle so that the head portion extends out of a single needle aperture at a distal end of the needle, said advancement causing the two or more arms to extend outward and perpendicular to the elongated portion;
    positioning the two or more arms adjacent to a tissue so that the suction opening on each of the two or more arms are located at the tissue; and
    applying suction through the suction lumen so to cause the two or more arms to suctionally engage the tissue at the suction opening.

10. The method of claim 9, wherein the tissue is located distal to the two or more arms relative to the elongated portion, and wherein the step of positioning is performed to distally advance the two or more arms toward the tissue so that the two or more arms contact the tissue.

11. The method of claim 9, wherein the tissue is located proximal to the two or more arms relative to the two or more arms, and wherein the step of positioning is performed to proximally retract the two or more arms toward the tissue so that the two or more arms contact the tissue.

12. The method of claim 9, further comprising the step of:
    performing an ablation procedure to the tissue using an ablation element of an ablation device while the two or more arms suctionally engage the tissue.

13. The method of claim 12, further comprising the step of:
    discontinuing suction through the suction lumen.

14. The method of claim 13, further comprising the step of:
    retracting the two or more arms of the tension apparatus into the needle, whereby the two or more arms within the needle are located proximal to the elongated portion of the tension apparatus.

* * * * *